United States Patent
Zeng

(10) Patent No.: US 10,758,895 B2
(45) Date of Patent: Sep. 1, 2020

(54) CU(I)-CATALYZED AZIDE-ALKYNE CYCLOADDITIONS (CUAAC) LIGANDS AND METHODS FOR CARRYING OUT CU(I)-CATALYZED AZIDE-ALKYNE CYCLOADDITION REACTIONS

(71) Applicant: UNIVERSITY OF PITTSBURGH—OF THE COMMONWEALTH SYSTEM OF HIGHER EDUCATION, Pittsburgh, PA (US)

(72) Inventor: Dexing Zeng, Pittsburgh, PA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 456 days.

(21) Appl. No.: 15/515,953

(22) PCT Filed: Sep. 30, 2015

(86) PCT No.: PCT/US2015/053342
§ 371 (c)(1),
(2) Date: Mar. 30, 2017

(87) PCT Pub. No.: WO2016/054277
PCT Pub. Date: Apr. 7, 2016

(65) Prior Publication Data
US 2017/0297008 A1 Oct. 19, 2017

Related U.S. Application Data

(60) Provisional application No. 62/057,986, filed on Sep. 30, 2014.

(51) Int. Cl.
| | |
|---|---|
| *A61K 9/00* | (2006.01) |
| *B01J 31/18* | (2006.01) |
| *A61K 49/00* | (2006.01) |
| *A61K 51/08* | (2006.01) |
| *A61K 51/10* | (2006.01) |
| *B01D 11/02* | (2006.01) |
| *C07D 249/04* | (2006.01) |
| *G01N 33/58* | (2006.01) |

(52) U.S. Cl.
CPC ....... *B01J 31/1815* (2013.01); *A61K 49/0032* (2013.01); *A61K 49/0039* (2013.01); *A61K 49/0056* (2013.01); *A61K 51/088* (2013.01); *A61K 51/1096* (2013.01); *B01D 11/0288* (2013.01); *C07D 249/04* (2013.01); *G01N 33/582* (2013.01); *B01J 2231/34* (2013.01); *B01J 2531/16* (2013.01)

(58) Field of Classification Search
CPC .................................................. B01J 31/1815
See application file for complete search history.

(56) References Cited

U.S. PATENT DOCUMENTS

| | | | |
|---|---|---|---|
| 5,463,082 | A | 10/1995 | Horvath et al. |
| 5,777,121 | A | 7/1998 | Curran et al. |
| 6,673,539 | B1 | 1/2004 | Wipf et al. |
| 7,060,850 | B2 | 6/2006 | Zhang et al. |
| 7,576,245 | B2 | 8/2009 | Zhang et al. |
| 7,875,752 | B2 | 1/2011 | Gladysz et al. |
| 8,148,287 | B2 | 4/2012 | Ying et al. |
| 2010/0197871 | A1 | 8/2010 | Finn et al. |
| 2013/0295019 | A1 | 11/2013 | Wu et al. |

OTHER PUBLICATIONS

Ozkal, Fine-Tunale Tris(triazolyl)methane Ligand for Copper(I)-Catalyzed Azide-Alkyne Cycloaddition Reactions, Adv. Synth, Catal, 2014, 356, 857-869.*
Del Amo, David Soriano, Biocompatible Copper(I) Catalysts for in Vivo Imaging of Glycans, J American Chemical Society, 2010, 16893-16899.
Besanceney-Webler, Christen, Increasing the Efficacy of Bioorthogonal Click Reactions for Bioconjugation: A Comparative Study, Angewandte Chemie Int. Ed., 2011, 50, 8051-8056.
Chan, Timothy R., Polytriazoles as Copper(I)-Stabilizing Ligands in Catalysis, American Chemical Society, 2004, vol. 6, No. 17, 2853-2855.
Sun, Lingyi, Highly-Efficient and Versatile Fluorous-Tagged Cu(I)-Catalyzed Azide-Alkyne Cycloaddition Ligand for Preparation of Bioconjugates, The Royal Society of Chemistry, 2013, 00, 1-5.
Zeng, Dexing, The Growing Impact of Bioorthogonal Click Chemistry on the Development of Radiopharmaceuticals, Journal of Nuclear Medicine, 2013, vol. 54, No. 6, 1-4.
Price, Eric W., Matching Chelators to Radiometals for Radiopharmaceuticals, Chem. Soc. Rev., 2014, 43, 260-290.
Form PCT/ISA/220, PCT Notification of Transmittal of the International Search Report and the Written Opinion of the International Search Authority, or the Declaration, PCT/US2015/053342, dated Nov. 25, 2015.
Form PCT/ISA/210, PCT International Search Report for International Application No. PCT/US2015/053342, dated Nov. 25, 2015.
Form PCT/ISA/237, PCT Written Opinion of the International Searching Authority for International Application No. PCT/US2015/053342, dated Nov. 25, 2015.
Pretze, Marc et al., Recent Trends in Bioorthogonal Click-Radiolabeling Reactions Using Fluorine-18, Molecules, Jul. 22, 2013, vol. 18, pp. 8618-8665.

(Continued)

*Primary Examiner* — Paul W Dickinson
(74) *Attorney, Agent, or Firm* — Paul D. Bangor, Jr.; Clark Hill, PLC

(57) ABSTRACT

A Cu(I)-Catalyzed Azide-Alkyne Cycloadditions (CuAAC) ligand comprising: a catalytic core; a fluorous tag; and a linker binding the fluorous tag to the catalytic core. A method for carrying out a Cu(I)-Catalyzed Azide-Alkyne Cycloaddition reaction, comprising: combining in a solution an alkyne-tagged component, an azide-tagged component and a Cu(I)-Catalyzed Azide-Alkyne Cycloadditions (CuAAC) ligand comprising: a catalytic core; a fluorous tag; and a linker binding the fluorous tag to the catalytic core; filtering the solution through a solid phase extraction filter to remove Cu(I)-ligand catalyst and/or excess ligand.

4 Claims, 5 Drawing Sheets

(56) References Cited

OTHER PUBLICATIONS

Berg, Regina et al., Advancements in the Mechanistic Understanding of the Copper-catalyzed Azide-alkyne Cycloaddition, Beilstein Journal of Orgainic Chemistry, Dec. 2, 2013, vol. 9, No. 1, pp. 2715-2750.

Fernandes, Anthony et al., Application of CuAAC for the Covalent Immobilization of Homogeneous Catalysts, Tetrahedron, Dec. 28, 2013, vol. 70, pp. 1709-1731.

* cited by examiner

CU(I)-CATALYZED AZIDE-ALKYNE CYCLOADDITIONS (CUAAC) LIGANDS AND METHODS FOR CARRYING OUT CU(I)-CATALYZED AZIDE-ALKYNE CYCLOADDITION REACTIONS

CROSS REFERENCE TO RELATED APPLICATIONS

This application claims the benefit of the filing date of U.S. provisional patent application Ser. No. 62/057,986, filed on Sep. 30, 2014, the entirety of which is incorporated herein by reference for all purposes.

STATEMENT REGARDING FEDERALLY SPONSORED RESEARCH OR DEVELOPMENT

This invention was made with government support under NIH grant # EB017317. The government has certain rights in the invention.

BACKGROUND OF THE DISCLOSURE

Click chemistry, particularly the copper(I)-catalyzed azide alkyne cycloaddition (CuAAC), has found applications in a wide range of modern chemistry-related areas, including organic chemistry, drug discovery, drug delivery and chemical biology. However, the toxicity of copper(I) from the generation of reactive nitrogen and oxygen species limits its application in living systems. For example, upon treatment of 1 mM $CuSO_4$, 1.5 mM sodium ascorbate, and 0.1 mM TBTA, Zebrafish embryos do not survive beyond 15 min. Therefore, the removal of copper species is typically required in order to avoid cytotoxicity caused by residual copper ions in biological applications, adding another layer of complexity to the application of CuAAC in living systems. To overcome the cumbersome copper removal problem, major efforts have been made to minimize the risk caused by this metal catalyst. New methodologies and techniques have been developed, including copper-free variants of azide-alkyne click chemistry (e.g., strain-promoted azide-alkyne cycloaddition (SPPAC) and resin-supported catalyst systems). However, these strategies cannot fulfill all the requirements due to their inherent deficiencies, including relatively sluggish kinetics in SPAAC and copper leaching problems observed in the resin-supported catalyst systems. Therefore, a more efficient approach is highly desired.

SUMMARY

The CuAAC catalytic ligands of the present disclosure enable rapid CuAAC of radioactive reactants in nanomolar scale, and it resulted in production of radiotracers in high radiochemical purity without observable transchelation and toxicity, which overcame major negative aspects of the commercially available CuAAC catalytic ligands.

The fluorous tagged tris(triazolylmethyl)amine-based Cu(I) stabilizing ligand ("FTBTT" or "FBTTBE") of the present disclosure facilitates the removal of toxic catalytic species while maintaining high catalytic efficiency. The use of a fluorous tag enables the easy separation of the toxic catalyst from the product (non-fluorous species) via the Fluorous Solid-Phase Extraction (F-SPE) approach, whereby the separation is accomplished by simply passing the reaction mixture through a fluorous resin. The bis(tert-butyltriazolyl) methyl amine based catalytic core shows significantly improved kinetics compared with two commercially available Cu(I) ligands, TBTA and THPTA. This new design of the catalytic ligand integrates homogenous solution phase reaction conditions with a phase-tag separation, while maintaining high reactivity as well as strong capacity to fully complex the copper ions. It is believed that the synergy of the fluorous-tag and the catalytic core in the designed FTBTT ligand will result in much broader applications of CuAAC The linker between the fluorous tag and catalytic core provides the necessary distance to reduce possible steric effects, and in the future it can be replaced by a hydrophilic linker to counter the loss of hydrophilic groups (i.e., the hydroxyl in THPTA) for improved aqueous solubility.

In order to solve the problems mentioned above for CuAAC and significantly increase synthesis yields of radiopharmaceuticals, the present disclosure discloses a series of novel Cu(I)-stabilizing ligands that combine the merits rendered by both fluorous separation tag and bis(tert-butyltriazoly)amine catalyst core Preferred ligands according to the present disclosure comprise three major components: (1) a bis(tert-butyltriazoly)amine core that catalyzes the CuAAC in much higher efficiency compared to TBTA and THPTA (two commercialized ligands); (2) a fluorous tag that allows rapid removal of the Cu(I)-ligand catalyst; and (3) a linker that serves as a spacer to tune the solubility and provide distance between the fluorous tag and catalytic core.

In a preferred aspect, the present disclosure comprises a Cu(I)-Catalyzed Azide-Alkyne Cycloadditions (CuAAC) ligand comprising: a catalytic core; a fluorous tag; and a linker binding the fluorous tag to the catalytic core.

In another preferred aspect of the CuAAC ligand, the catalytic core comprises bis(alkyl-triazoly)amine.

In yet another preferred aspect of the CuAAC ligand, the catalytic core comprises -2-[4-{bis[(1-tert-butyl-1H-1,2,3-tri-azol-4-yl)methyl]amino)methyl}-1H-1,2,3-triazol-1-yl]).

In still another preferred aspect, the CuAAC ligand comprises one of:

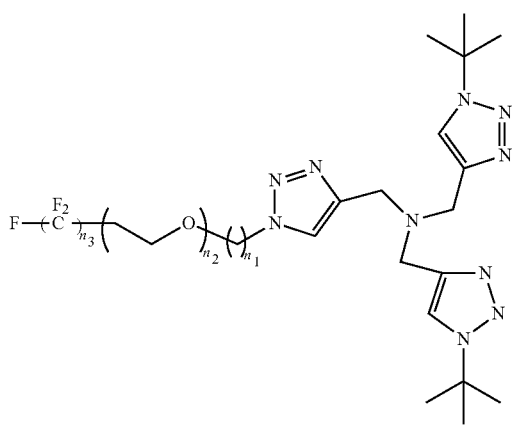

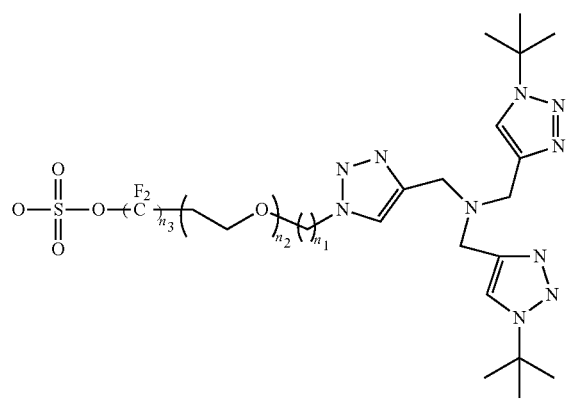
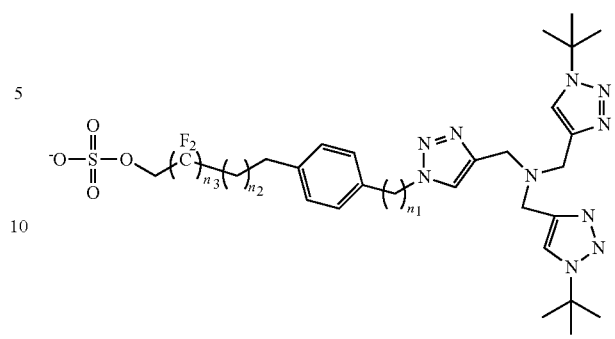
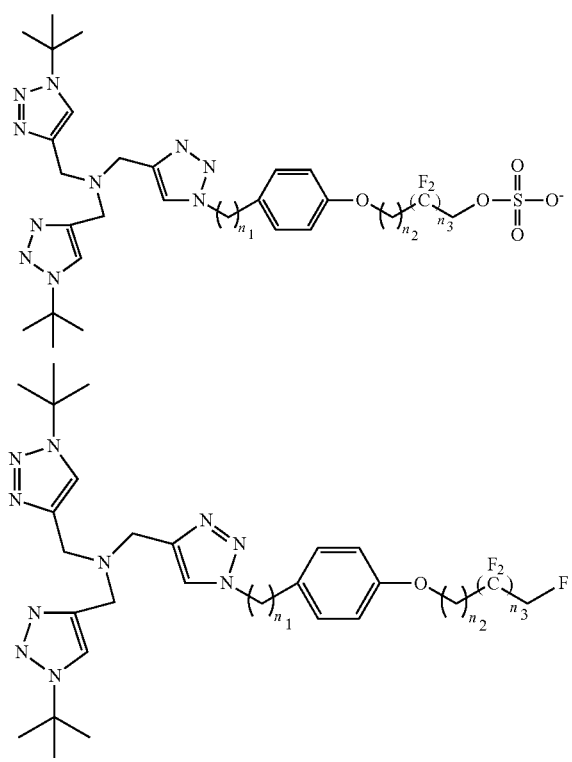
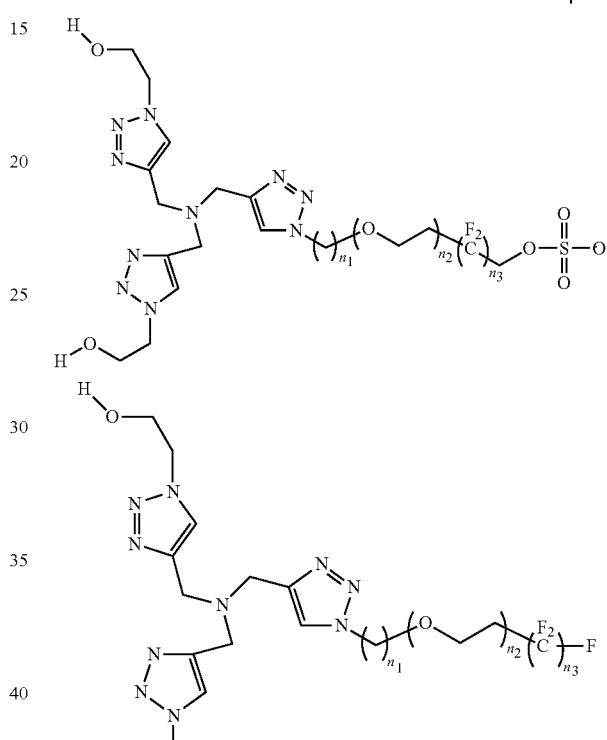
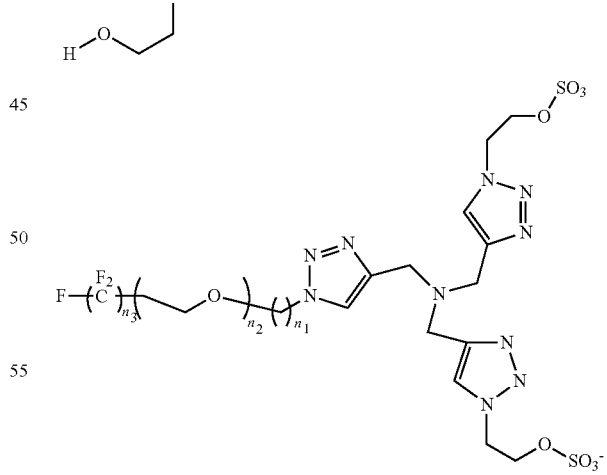
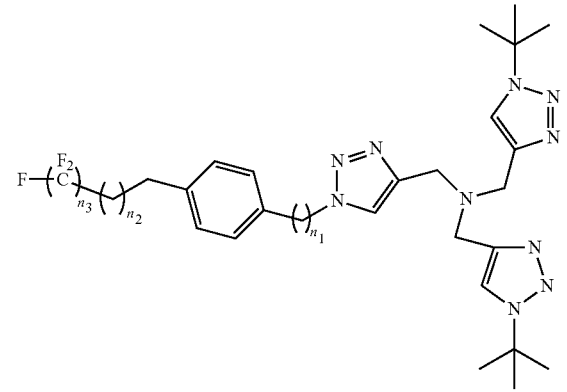

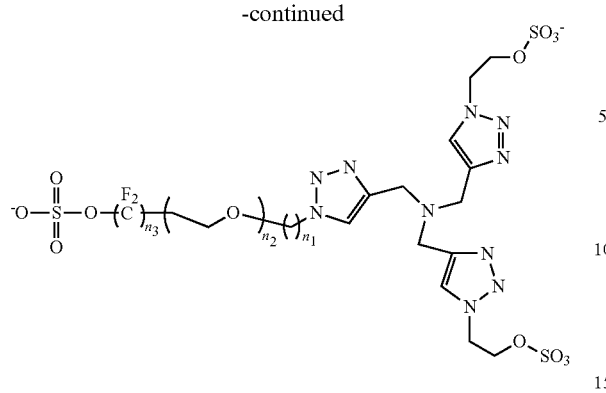

Wherein $n_1$, $n_2$ and $n_3$ are independent $n_1$=1, 2, 3; $n_2$=0, 2, 4; $n_3$=2, 3, 4, 5, 6, 7, 8;

wherein $n_1$, $n_2$, and $n_3$ are independently the same or different at each occurrence and wherein $n_1$ is an integer from 1-3; $n_2$ is an integer 0, 2 or 4 and $n_3$ is an integer from 2-8.

In yet another preferred aspect of the CuAAC ligand, the values for $n_1$, $n_2$, and $n_3$ are selected from the group consisting of: (1) $n_1$=1, $n_2$=0, $n_3$=2, 3, 4, 5, 6, 7 or 8; (2) $n_1$=2, $n_2$=0, $n_3$=2, 3, 4, 5, 6, 7 or 8; (3) $n_1$=3, $n_2$=0, n3=2, 3, 4, 5, 6, 7 or 8; (4) $n_1$=1, n2=2, $n_3$=2, 3, 4, 5, 6, 7 or 8; (5) $n_1$=2, $n_2$=2, n3=2, 3, 4, 5, 6, 7 or 8; (6) $n_1$=3, n2=2, $n_3$=2, 3, 4, 5, 6, 7 or 8; (7) $n_1$=1, $n_2$=4, n3=2, 3, 4, 5, 6, 7 or 8; (8) $n_1$=2, n2=4, $n_3$=2, 3, 4, 5, 6, 7 or 8; (9) $n_1$=3, $n_2$=4, n3=2, 3, 4, 5, 6, 7 or 8.

In another preferred aspect of the CuAAC ligand, the fluorous tag allows for rapid removal of the Cu(I)-ligand catalyst.

In yet a further preferred aspect of the CuAAC ligand, the linker comprises PEG.

In another preferred aspect of the CuAAC ligand, the linker is selected to tune the solubility of the CuAAC ligand in a reaction solution.

In another preferred aspect, the present disclosure comprises a method for carrying out a Cu(I)-Catalyzed Azide-Alkyne Cycloaddition reaction, comprising: combining in a solution an alkyne-tagged component, an azide-tagged component and a Cu(I)-Catalyzed Azide-Alkyne Cycloadditions (CuAAC) ligand comprising: a catalytic core; a fluorous tag; and a linker binding the fluorous tag to the catalytic core, filtering the solution through a solid phase extraction filter to remove Cu(I)-ligand catalyst and/or excess ligand.

In another preferred aspect of the method for carrying out a Cu(I)-Catalyzed Azide-Alkyne Cycloaddition reaction, the catalytic core comprises bis(alkyl-triazolyl)amine.

In another preferred aspect of the method for carrying out a Cu(I)-Catalyzed Azide-Alkyne Cycloaddition reaction, the catalytic core comprises -2-[4-{bis[(1-tert-butyl-1H-1,2,3-tri-azol-4-yl) methyl]amino)methyl}-1H-1,2,3-triazol-1-yl]).

In another preferred aspect of the method for carrying out a Cu(I)-Catalyzed Azide-Alkyne Cycloaddition reaction, the (CuAAC) ligand comprises one of:

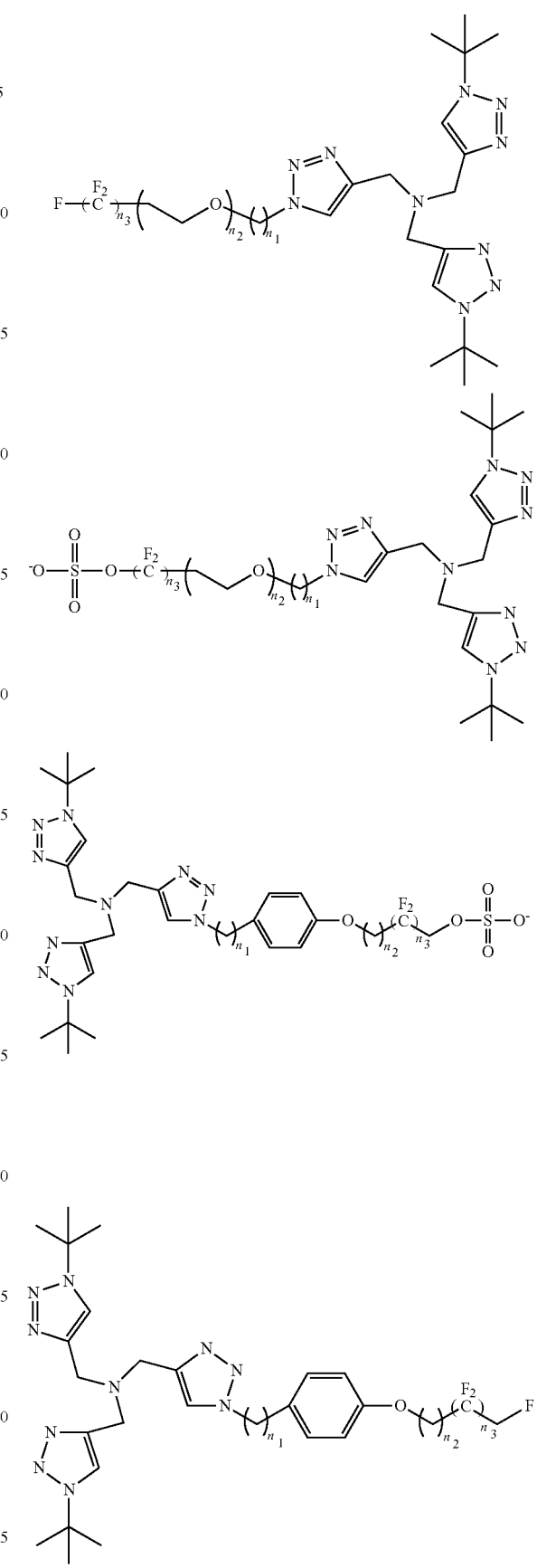

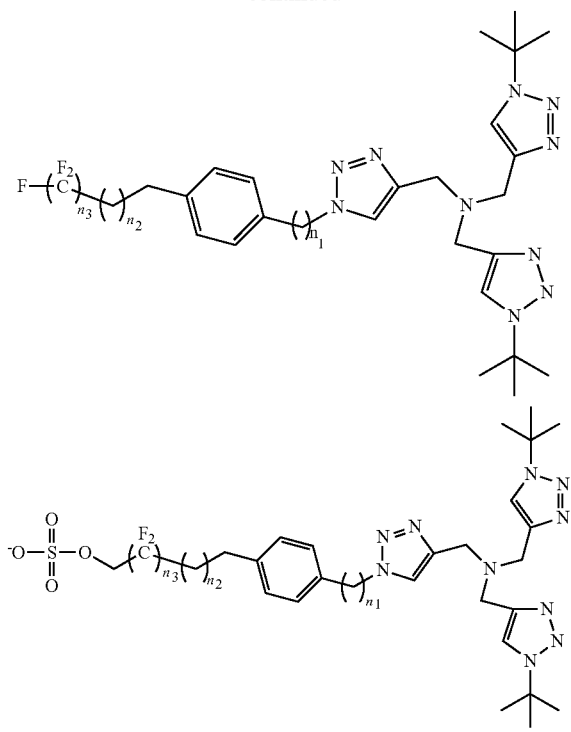
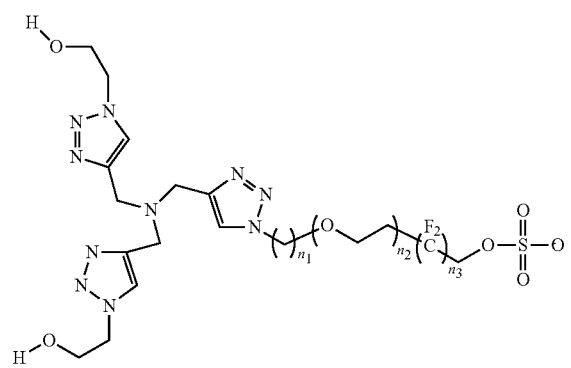
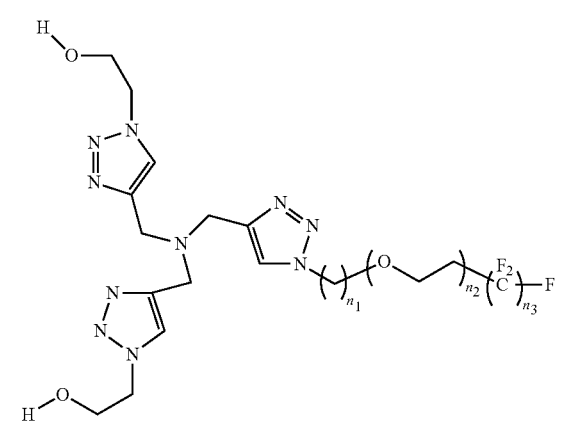

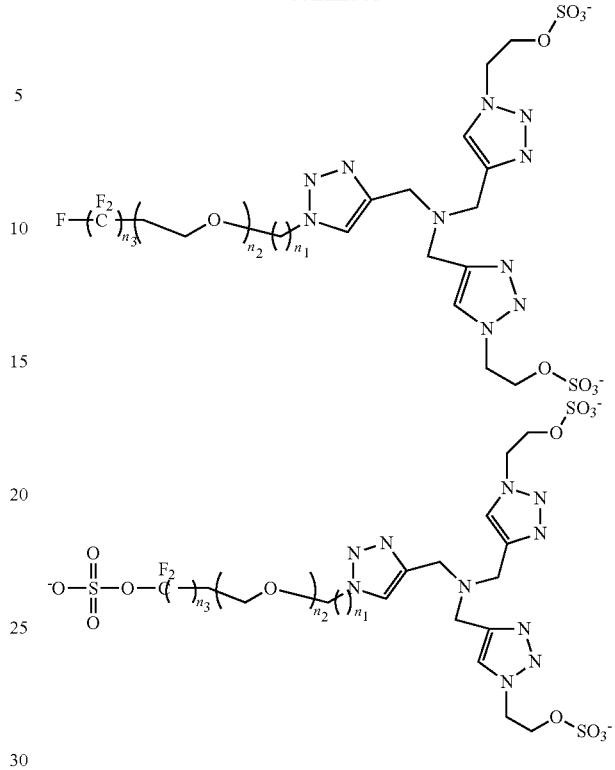

Wherein $n_1$, $n_2$ and $n_3$ are independent $n_1=1, 2, 3$; $n_2=0, 2, 4$; $n_3=2, 3, 4, 5, 6, 7, 8$;

wherein $n_1$, $n_2$ and $n_3$ are independently the same or different at each occurrence and wherein $n_1$ is an integer from 1-3; $n_2$ is an integer 0, 2 or 4 and $n_3$ is an integer from 2-8.

In another preferred aspect of the method for carrying out a Cu(I)-Catalyzed Azide-Alkyne Cycloaddition reaction, the values for $n_1$, $n_2$ and $n_3$ for the CuAAC ligand are selected from the group consisting of (1) $n_1=1$, $n_2=0$, $n_3=2, 3, 4, 5, 6, 7$ or 8; (2) $n_1=2$, $n_2=0$, $n_3=2, 3, 4, 5, 6, 7$ or 8; (3) $n_1=3$, $n_2=0$, n3=2, 3, 4, 5, 6, 7 or 8; (4) $n_1=1$, n2=2, $n_3=2, 3, 4, 5, 6, 7$ or 8; (5) $n_1=2$, $n_2=2$, n3=2, 3, 4, 5, 6, 7 or 8; (6) $n_1=3$, n2=2, $n_3=2, 3, 4, 5, 6, 7$ or 8; (7) $n_1=1$, $n_2=4$, n3=2, 3, 4, 5, 6, 7 or 8; (8) $n_1=2$, n2=4, $n_3=2, 3, 4, 5, 6, 7$ or 8; (9) $n_1=3$, $n_2=4$, n3=2, 3, 4, 5, 6, 7 or 8.

In yet another preferred aspect of the method for carrying out a Cu(I)-Catalyzed Azide-Alkyne Cycloaddition reaction, the fluorous tag allows for rapid removal of Cu(I)-ligand catalyst and/or excess ligand.

In another preferred aspect of the method for carrying out a Cu(I)-Catalyzed Azide-Alkyne Cycloaddition reaction, the linker is selected to tune the solubility of the CuAAC ligand in the solution.

In yet a further preferred aspect of the method for carrying out a Cu(I)-Catalyzed Azide-Alkyne Cycloaddition reaction, the alkyne-tagged component comprises an alkyne-bearing radiometal having a radiometal selected from the group consisting of copper (Cu), gallium (Ga), scandium (Sc), indium (In), lutetium (Lu), yttrium (Y), zirconium (Zr), bismuth (bi), lead (Pb), and actinium (Ac).

In another preferred aspect of the method for carrying out a Cu(I)-Catalyzed Azide-Alkyne Cycloaddition reaction, the azide-tagged component comprises an azide-tagged pharmaceutical agent.

In still another preferred aspect of the method for carrying out a Cu(I)-Catalyzed Azide-Alkyne Cycloaddition reaction, the azide-tagged pharmaceutical agent comprises a compound selected from the group consisting of a small molecule, a peptide and an monoclonal antibody (mAbs).

In another preferred aspect, the method for carrying out a Cu(I)-Catalyzed Azide-Alkyne Cycloaddition reaction further comprises producing the alkyne-tagged component comprising an alkyne-bearing radiometal with a chelator selected from the group consisting of a NOTA, a DOTA, a CB-TE2A, a CB-DO2A, a 3p-C-DEPA, a TCMC, and Oxo-DO3A, a TETA, a TE2A, a CB-TE1A1P, a CB-TE2P, MM-TE2A, a DM-TE2A, a NETA, a TACN-TM, a DTPA, a 1B4M-DTPA, a CHX-A"-DTPA, a TRAP (PRP9), a NOPO, an AAZTA and derivatives (DATA), a HBED, a SHBED, a BPCA, a CP256, a Desferrioxamine (DFO), an $H_6$phospa, a PCTA, a HEHA, a PEPA, an $H_2$dedpa, an $H_4$octapa, an $H_2$azapa, an $H_5$decapa.

In another preferred aspect of the method for carrying out a Cu(I)-Catalyzed Azide-Alkyne Cycloaddition reaction, the solid phase extraction filter comprises a fluorous resin or a solid phase extraction filter.

BRIEF DESCRIPTION OF THE DRAWINGS

The present disclosure is illustrated by way of example and not limitation in the figures of the accompanying drawings, in which.

DETAILED DESCRIPTION

It is to be understood that the descriptions of the present disclosure have been simplified to illustrate elements that are relevant for a clear understanding of the present disclosure, while eliminating, for purposes of clarity, other elements that may be well known. Those of ordinary skill in the art will recognize that other elements are desirable and/or required in order to implement the present disclosure. However, because such elements are well known in the art, and because they do not facilitate a better understanding of the present disclosure, a discussion of such elements is not provided herein. Additionally, it is to be understood that the present disclosure is not limited to the embodiments described herein, but encompasses any and all embodiments within the scope of the description and the following claims.

Cu(I)-Catalyzed Azide-Alkyne Cycloadditions (CuAAC) are regarded as an ubiquitous chemical tool with applications in nearly all areas of modern chemistry, including drug discovery, bioconjugation, nanoscience and radiopharmaceuticals. However, the Cu(I) catalyst used in CuAAC is problematic, especially in biological systems due to the relatively low catalytic efficiency and possible toxicity of copper. Therefore, significant efforts have been dedicated towards the development of Cu(I)-stabilizing ligands that can accelerate the reaction by a few orders of magnitude The application of CuAAC is particularly challenging for producing metal-based radiopharmaceuticals, since even for an optimized Cu(I)-ligand catalytic system, there is significant transchelation between copper catalyst and labeled/unlabeled chelators, as well as a very slow reaction rate due to working with nanomolar concentrations of radioactive reactants Moreover, the toxicity of the species (copper and ligand) in this catalytic system remains an unsolved issue for biological and/or medical applications.

In order to solve the problems mentioned above for CuAAC and significantly increase synthesis yields of radiopharmaceuticals, the present disclosure discloses a series of novel Cu(I)-stabilizing ligands that combine the merits rendered by both fluorous separation tag and bis(tert-butyltriazoly)amine catalyst core. Preferred ligands according to the present disclosure comprise three major components: 1) a bis(tert-butyltriazoly)amine core that catalyzes the CuAAC in much higher efficiency compared to TBTA and THPTA (two commercialized ligands); 2) a fluorous tag that allows rapid removal of the Cu(I)-ligand catalyst; and 3) a linker that serves as a spacer to tune the solubility and provide distance between the fluorous tag and catalytic core.

Figure 1:
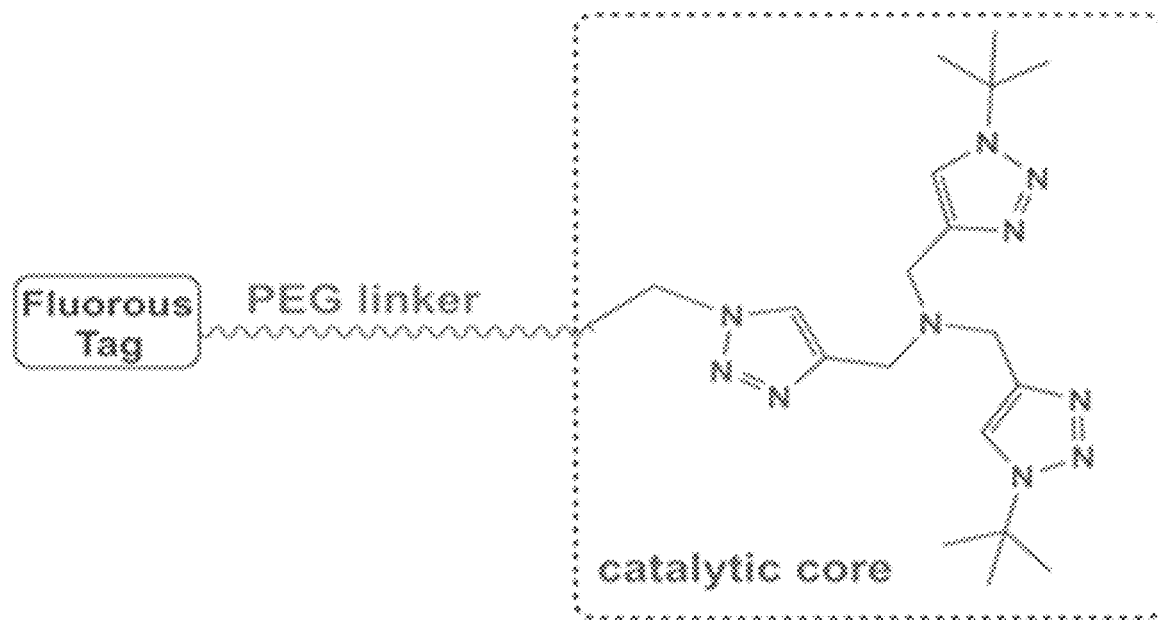
FIG. 1 shows the developed CuAAC catalyst according to the present disclosure (also referred as "Cu(I) stabilizing ligands") and/or "FTBTT" (Fluorous Tagged -2-[4-{(Bis[(1-Tert-butyl-1H-1,2,3-Tri-azol-4-yl)methyl]amino)methyl}-1H-1,2,3-triazol-1-yl]).

FIG. 1 shows the developed CuAAC catalyst according to the present disclosure (also referred as "Cu(I) stabilizing ligands") and/or "FTBTT" (Fluorous Tagged -2-[4-{(Bis{(1-Tert-butyl-1H-1,2,3-Tri-azol-4-yl)methyl]amino) methyl}-1H-1,2,3-triazol-1-yl]).

By using these newly developed ligands, radiometal labeled peptides have been successfully prepared rapidly (~10 min) without observable copper transchelation, and moreover, the toxic catalyst was removed by simply passing through a Sep-Pak solid-phase extraction (SPE).

Figure 2:
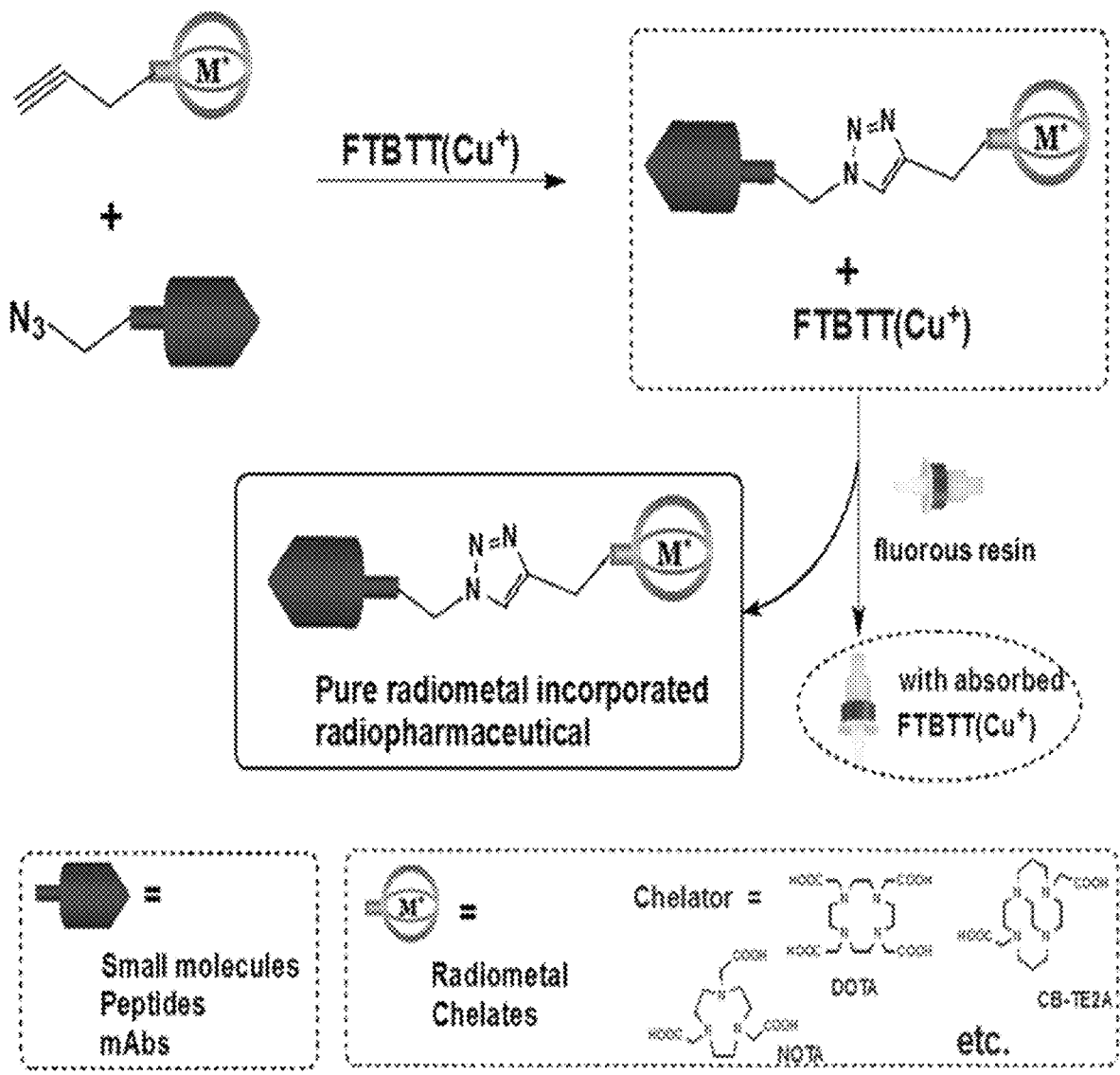
FIG. 2 shows a preferred generic scheme (Scheme 1) according to the present disclosure of the FTBTT catalyzed click reaction for the preparation of radiometal-based radiopharmaceuticals.

FIG. 2 shows a preferred generic scheme (Scheme 1) according to the present disclosure of the FTBTT catalyzed click reaction for the preparation of radiometal-based radiopharmaceuticals.

The novel compounds according to the present disclosure, along with optimized agents, will have a significant impact for the field metal-based radiopharmaceuticals, which is an emerging area of agents for positron emission tomography (PET). In addition, the strategy and agents described above can be applied to the rapid synthesis of bioconjugates that incorporate dyes for optical imaging, therapeutic radiometals (such as 90Y, 213Bi, 225Ac or 177Lu) or other types of drug molecules.

The preferred CuAAC catalytic ligands of the present disclosure combine the merits rendered by a fluorous separation tag and bis(tert-butyltriazoly)amine catalyst core. The advantages include: 1) the ability to catalyze CuAAC in orders of magnitude greater efficiency compared to TBTA and THPTA (two commercially available ligands) as shown in the comparison graphs below; 2) rapid removal of the toxic species (copper and ligand) from the CuAAC catalytic system by passing through a Sep-Pak SPE (minimizing the Cu(I) transchelation is extremely critical for radiometal-based pharmaceuticals, as non-radioactive copper contaminates will dramatically adversely affect (or completely disable) the corresponding radiopharmaceuticals); and 3) the ability to tune the solubility using different linkers.

Figure 3:
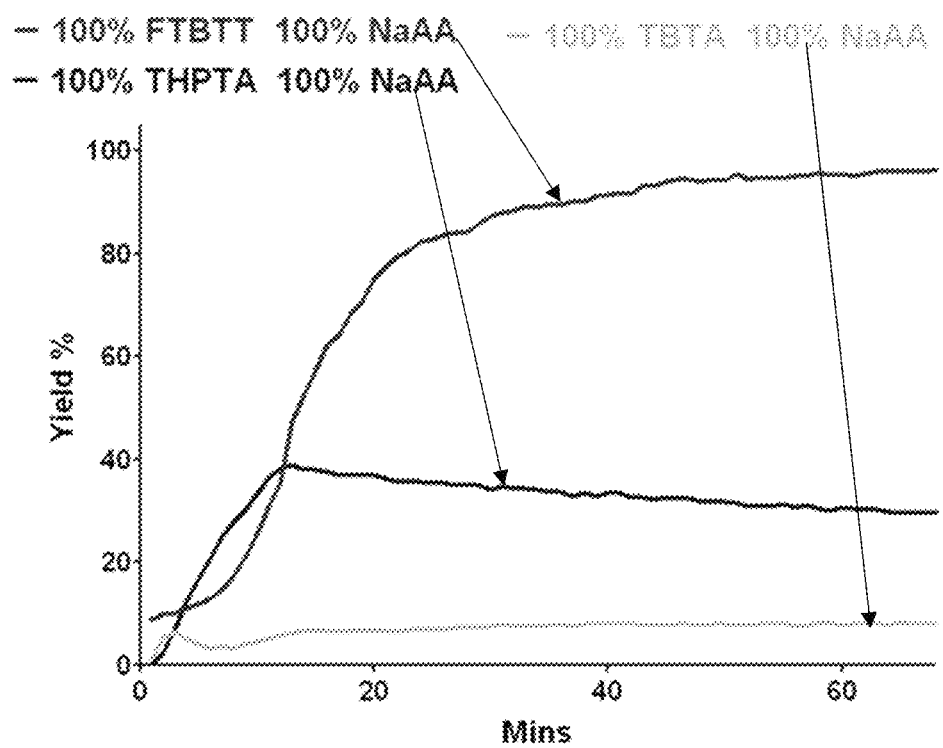
FIG. 3 shows Comparison Graph 1 which is a comparison of the Cu(I) stabilizing ligands: ([azidocoumarin]=10 μM; [propargyl alcohol]=15 μM, ligand: Cu(II)=1.5:1).

Comparison Graph 1 of FIG. 3 shows a comparison of the Cu(I) stabilizing ligands: ([azidocoumarin]=10 μM; [propargyl alcohol]=15 μM, ligand: Cu(II)=1.5:1).

Comparison Graph 1 of FIG. 3 shows 100% FTBTT 100% NaAA (highest Yield %); 100% THPTA 100% NaAA ($2^{nd}$ lowest Yield %); 100% TBTA 100% NaAA (lowest Yield %).

Figure 4:
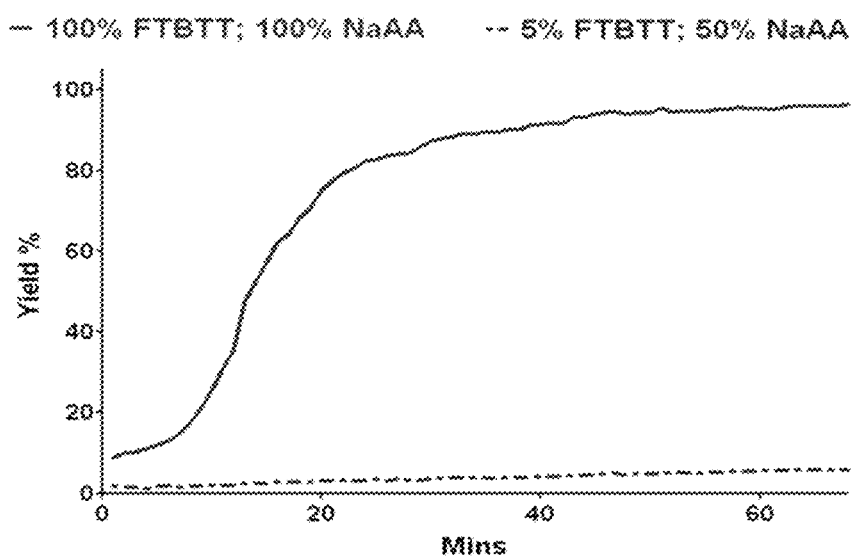
FIG. 4 shows Comparison Graph 2 illustrating that after the FTBTT ligand catalyzed radiolabelings (took 15 min), 80% of the resulting product (Cu-64 incorporated peptide) could be eluted out as product, and the radiopurity were greater than 95%.

Comparison Graph 2 of FIG. 4 shows that after the FTBTT ligand catalyzed radiolabelings (took 15 min), 80% of the resulting product (Cu-64 incorporated peptide) could be eluted out as product, and the radiopurity were greater than 95%.

The preferred methods and ligands/reagents of the present disclosure will enable rapid CuAAC of nanomolar radioactive reactants in high radiochemical purity and yield with minimal toxicity, which will overcome the negative aspects of the commercially available CuAAC catalytic ligands.

Although significant efforts have been dedicated towards the development of catalytic ligands with high catalytic efficiency, the possible metal transchelation and toxicity of traditional catalytic system remain an unsolved issue for biological and/or biomedical applications. The preferred CuAAC catalytic ligands of the present disclosure overcome these problems, and they have been successfully tested in the rapid synthesis of biomedical-related conjugates such as, optical imaging, positron emission tomography (PET) imaging, and radiation therapeutic agents. The unique features of the preferred CuAAC catalytic ligands of the present disclosure include: 1) Elimination of metal transchelation between copper catalyst and labeled/unlabeled chelators in the radiopharmaceuticals; 2) The ability to catalyze CuAAC with much greater efficiency in the orders of magnitude compared to TBTA and THPTA (two commercially available ligands); 3) Rapid removal of the toxic species (copper and ligand) from the CuAAC catalytic system.

Preferred FTBTT ligands according to the present disclosure may comprise fluorous tags, linkers and catalytic cores according to the preferred structures:

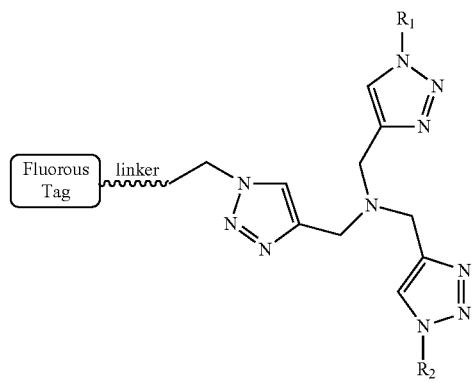

Wherein R1 and R2 are independently

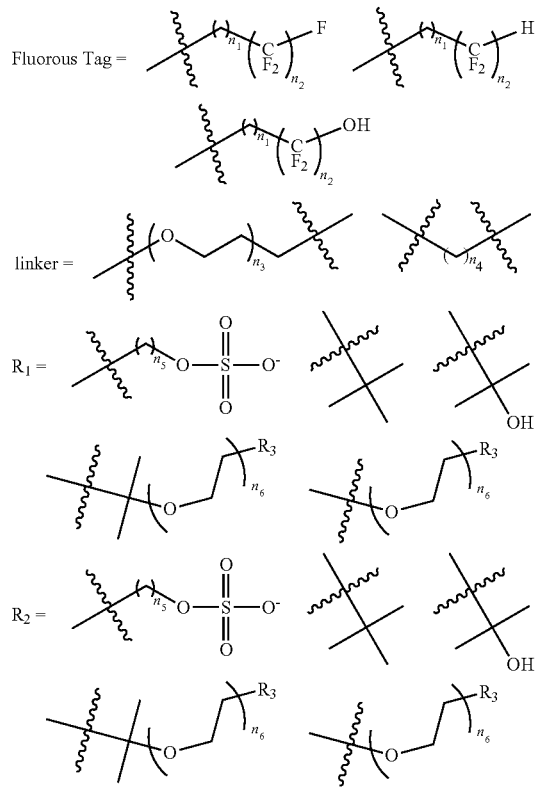

Wherein n1, n2, n3, n4, n5, and n6 are independently $R_3$=H, OH or $NH_2$

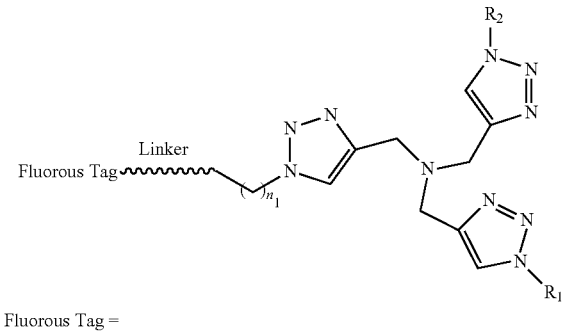

Fluorous Tag =

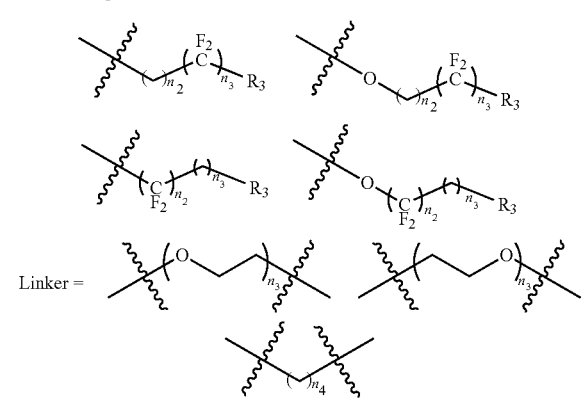

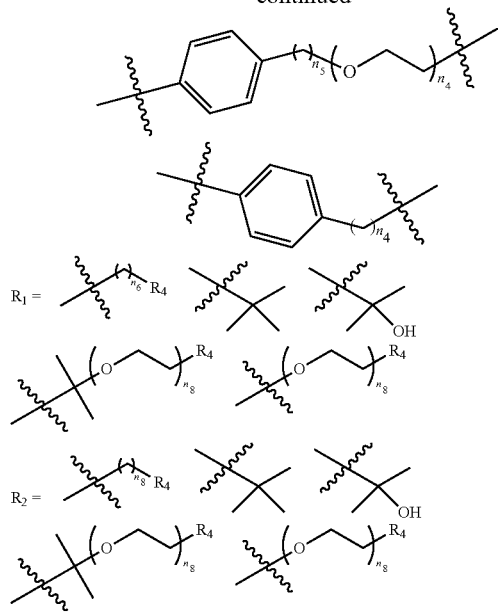
$R_3$ = F, H, OH, $NH_2$, COOH, $SO_3$-, $OSO_3$-
$R_4$ = H, OH, $NH_2$, COOH, $SO_3$-, $OSO_3$-
Wherein $R_3$ and $R_4$ are independently, the same or different, one of F, H, OH, $NH_2$, COOH, $SO_3$—, and —$OSO_3$— and wherein n1, n2, n3, n4, n5 and n6 meant to be "independently the same or different at each occurrence.
FTBTT ligands according to the present disclosure preferably comprise:
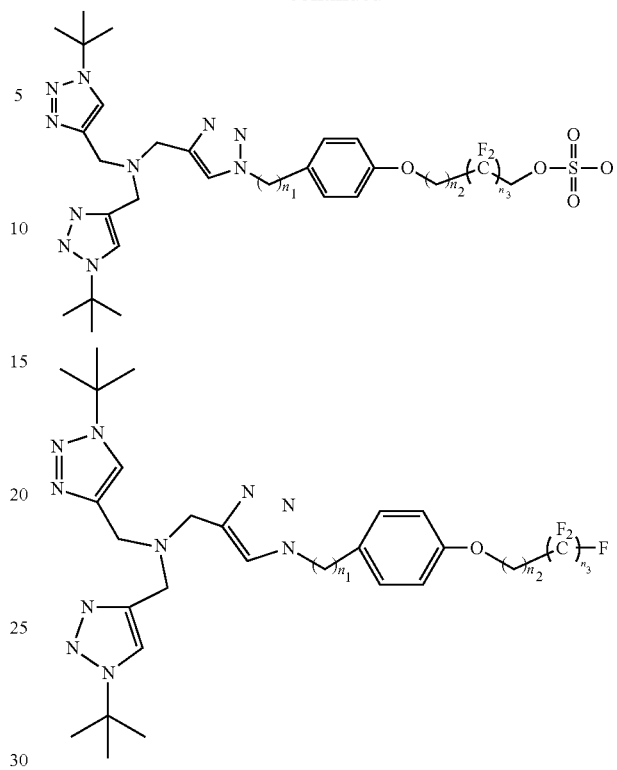
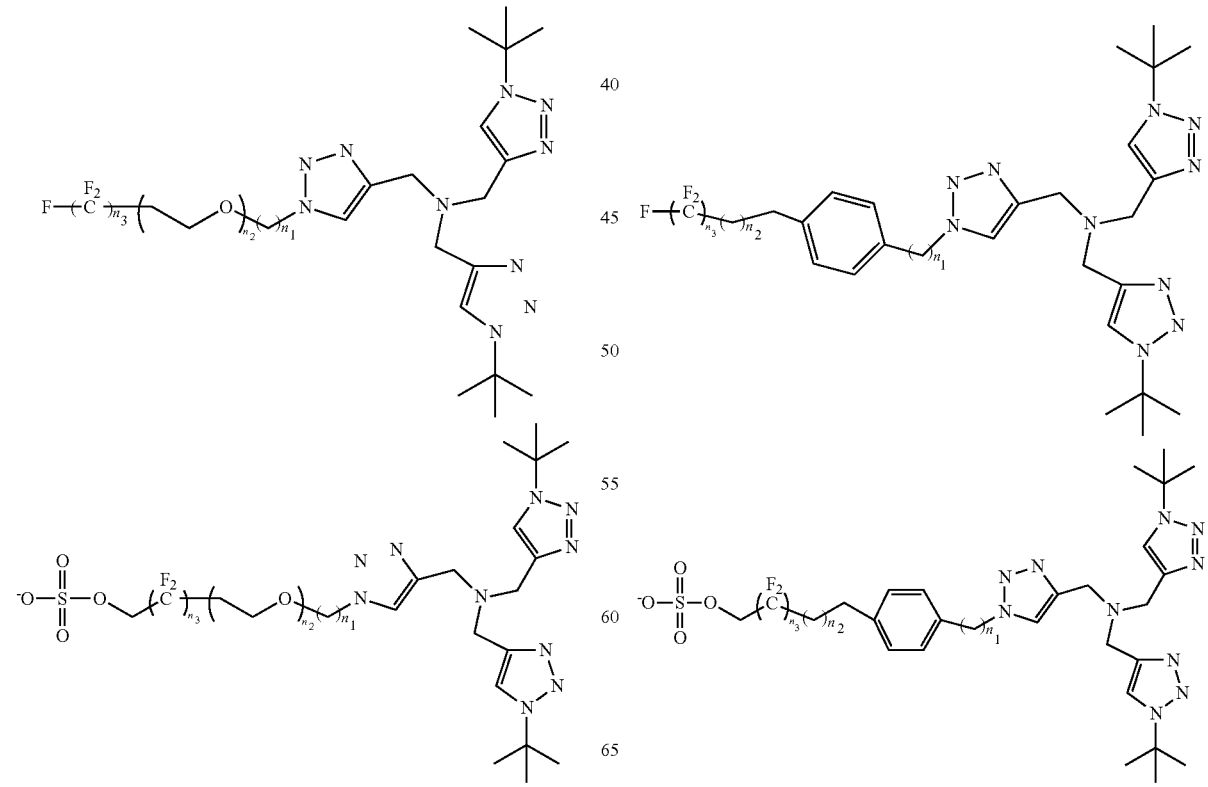

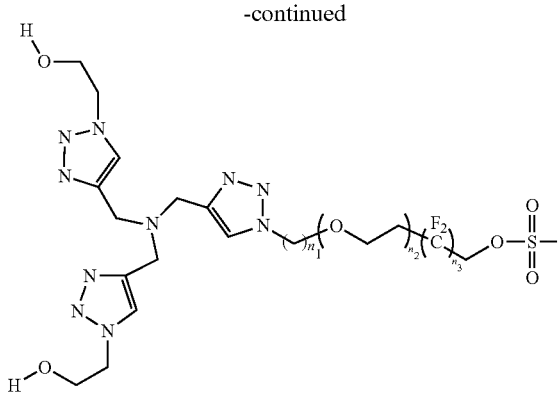
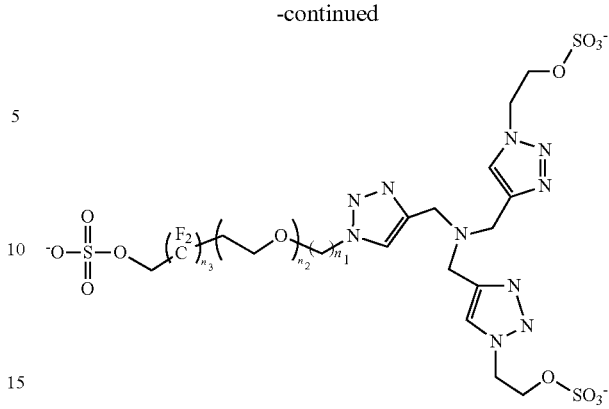

Wherein $n_1$, $n_2$ and $n_3$ are independent $n_1$=1, 2, 3; $n_2$=0, 2, 4; $n_3$=2, 3, 4, 5, 6, 7, 8;

Wherein $n_1$, $n_2$, and $n_3$, are independently the same or different at each occurrence and wherein $n_1$ preferably is an integer from 1-3; $n_2$ preferably is an integer 0, 2 or 4; and $n_3$ preferably is an integer from 2-8; and further wherein the values for $n_1$, $n_2$, and $n_3$ are: (1) $n_1$=1, $n_2$=0, n3=2, 3, 4, 5, 6, 7 or 8; (2) $n_1$=2, $n_2$=0, $n_3$=2, 3, 4, 5, 6, 7 or 8; (3) $n_1$=3, $n_2$=0, $n_3$=2, 3, 4, 5, 6, 7 or 8; (4) $n_1$=1, $n_2$=2, $n_3$=2, 3, 4, 5, 6, 7 or 8; (5) $n_1$=2, $n_2$=2, $n_3$=2, 3, 4, 5, 6, 7 or 8; (6) $n_1$=3, $n_2$=2, $n_3$=2, 3, 4, 5, 6, 7 or 8; (7) $n_1$=1, $n_2$=4, $n_3$=2, 3, 4, 5, 6, 7 or 8; (8) $n_1$=2, $n_2$=4, $n_3$=2, 3, 4, 5, 6, 7 or 8; (9) $n_1$=3, $n_2$=4, $n_3$=2, 3, 4, 5, 6, 7 or 8.

A preferred scheme (Scheme 2) of Cu(I)-Catalyzed Azide-Alkyne Cycloaddition reagents for use in preferred methods for carrying out a Cu(I)-Catalyzed Azide-Alkyne Cycloaddition reactions using an FTBTT(Cu$^+$) stabilizing ligand according to the present disclosure are shown in Scheme 2 wherein $R_1$ preferably may comprise one of propargylamine, Cyclo(RGDyK) or AE105 and $R_2$ preferably may comprise one of Cy3-N3, 7-hydroxycoumarin-N3 or ($^{64}$Cu)CB-TE1K1P.

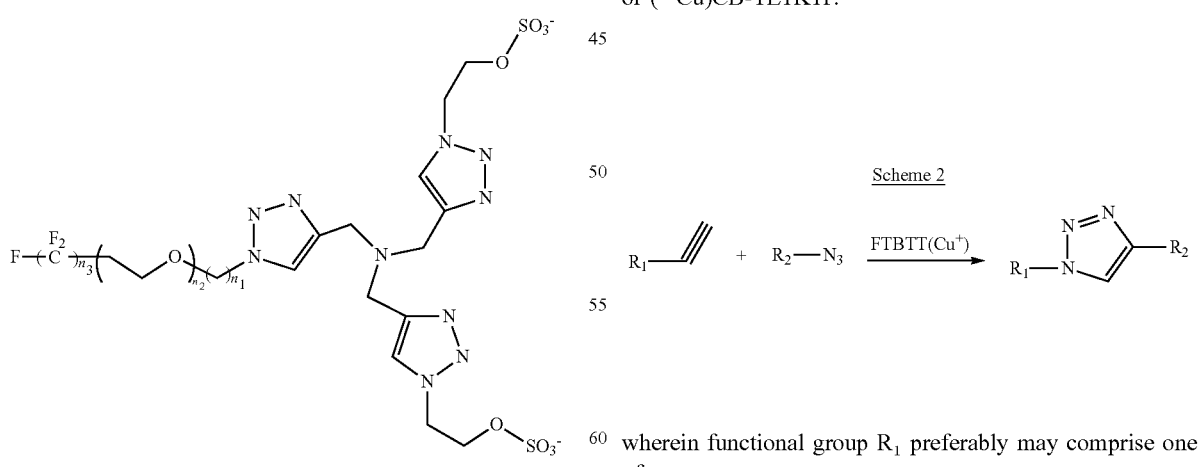

Scheme 2 wherein functional group $R_1$ preferably may comprise one of:

Propargylamine

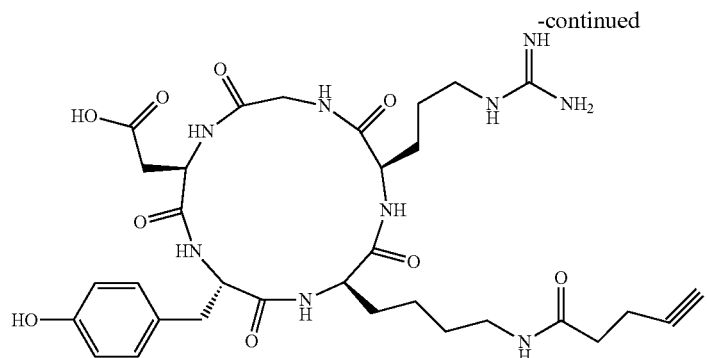
Cyclo(RGDyK)

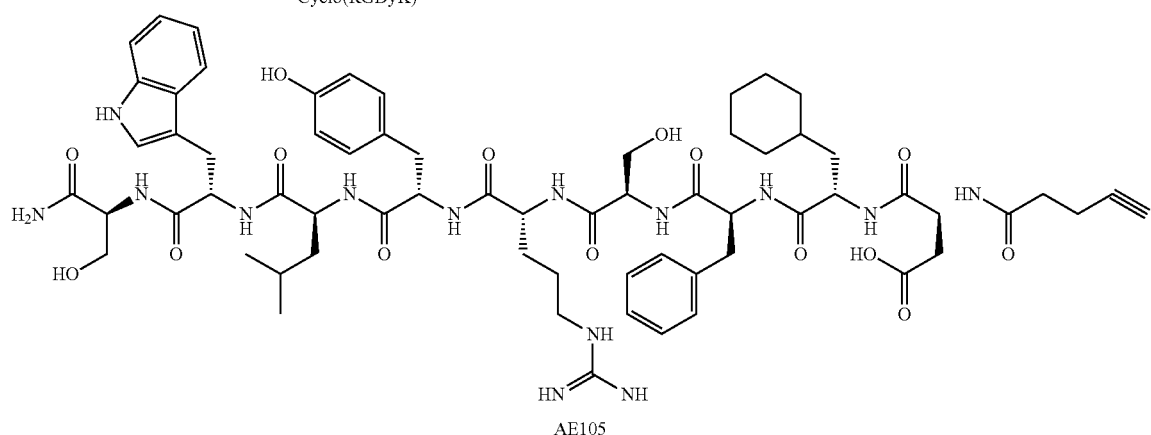
AE105 and wherein functional group R₂ preferably may comprise one of:

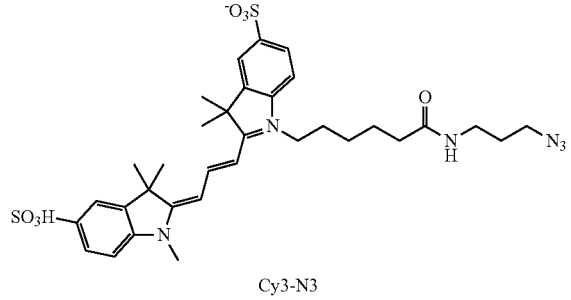
Cy3-N3

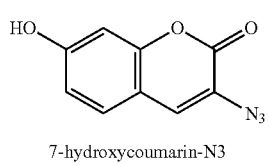
7-hydroxycoumarin-N3

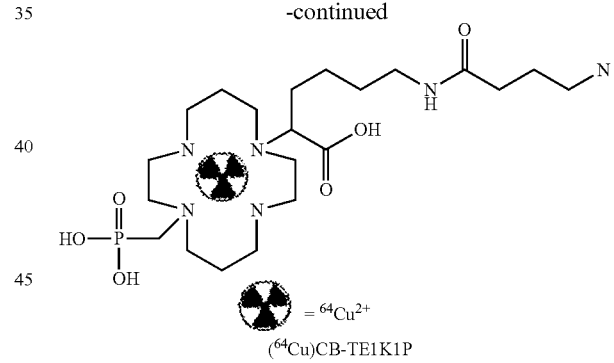
($^{64}$Cu)CB-TE1K1P

The ligand according to the present disclosure (FTBTT) for Cu(I)-Catalyzed Azide-Alkyne Cycloaddition (CuAAC) FTBTT demonstrates not only superior catalytic efficiency but also the ease of removing toxic copper species FTBTT has also been successfully applied in the synthesis of radiometal-labeled peptide and antibody without observable transchelation with the non-radioactive Cu(I) catalyst.

In our study, a model FTBTT ligand was synthesized via multiple steps (Scheme 3). Alcohol 1 was treated with sodium azide to generate azide 2. Subsequently, 2 was reacted with 3,3-diethoxy-1-propyne through a copper catalyzed click reaction to give the corresponding triazole 3, which was then converted to the. triazolylcarbaldehyde 4 via TFA (trifluoroacetic acid) treatment. Facilitated by the reduction reagent NaBH(OAc)₃, intermediate 5 was then prepared through the reaction between 4 and propargyl amine.[17] Intermediate 7 was synthesized by treating the alcohol 6 first with thionyl chloride, followed by azidation using sodium azide. In the final step, the FTBTT ligand 8 was obtained through the click reaction between 5 and 7.

In order to validate its improved catalytic efficiency, the reactivity of the synthesized FTBTT ligand was then compared with two widely used ligands TBTA and THPTA. Specifically, we compared the relative reactivity of the canonical Cu(I) catalysts in the form of TBTA-Cu(I), THPTA-Cu(I) and FTBTT-Cu(I) via a reported fluorogenic assay 18 based on the reaction between propargyl amine and 3-azido-7-hydroxycoumarin (Scheme 4). Upon formation of the triazole ring, strong fluorescence at 477 nm can be quantitatively measured to determine the extent of the reaction. FTBTT showed the greatest ability to accelerate CuAAC, followed by THPTA, with TBTA having the lowest reactivity (Comparison Graph 3). The reaction catalyzed by Cu(I)—FTBTT completed in around 20 min at ambient temperature using 50 μM of Cu(I) and 1.5 eq. (75 μM) of FTBTT. In contrast, no more than 40% yield was achieved after 12 h with the TBTA and THPTA ligands. This implies that FTBTT renders a much higher catalytic capacity in CuAAC compared with TBTA and THPTA, indicating that the catalytic core maintains good reactivity after the attachment of the fluorous tag.

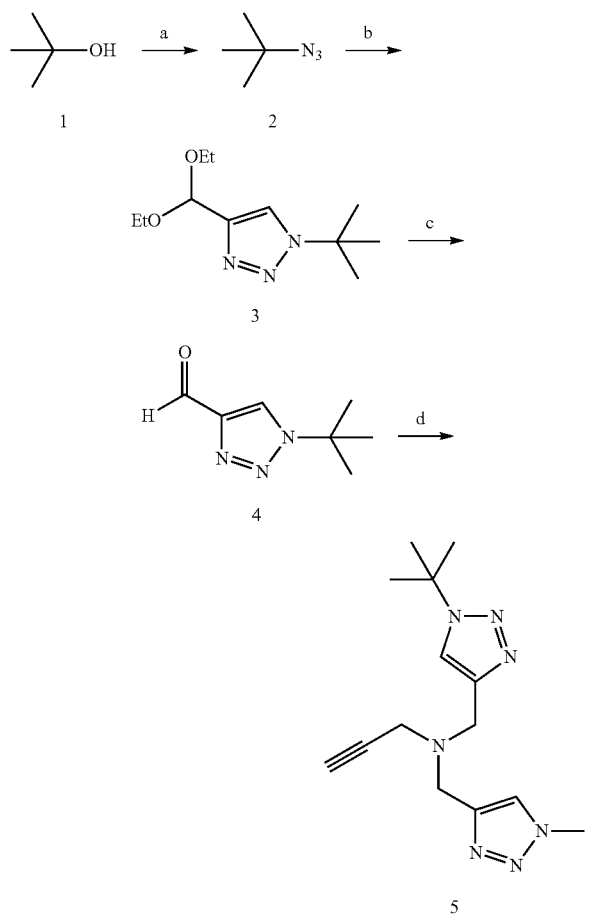

Scheme 3. Synthesis of the FTBTT ligand.

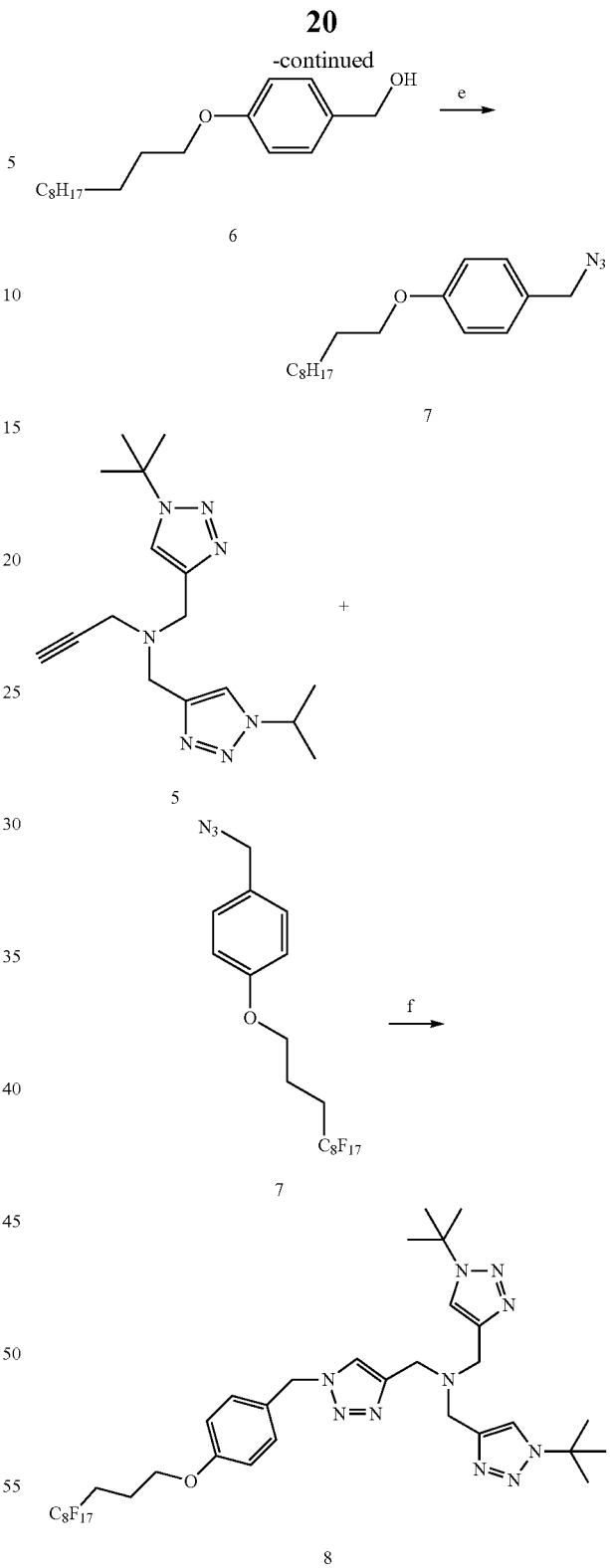

Reagents and conditions: (a) NaN3, H$_2$SO$_4$:H$_2$O = 1:1 (w/w); (b) 3,3-diethoxy-1-propyne, NaHCO$_3$, CuSO$_4$, sodium ascorbate (NaAA), t-BuOH:H$_2$O = 1:1 (v/v); (c) TFA, DCM:H$_2$O = 2:1 (v/v); (d) propargyl amine, NaBH(OAc)$_3$ Dichloroethane; (e) 1). SOCl$_2$, DMF, 2). NaN$_3$, DMF:THF - 1:1 (v/v); (f) CuSO$_4$, NaAA, t-BuOH:H$_2$O = 1:1 (v/v).

Figure 5:
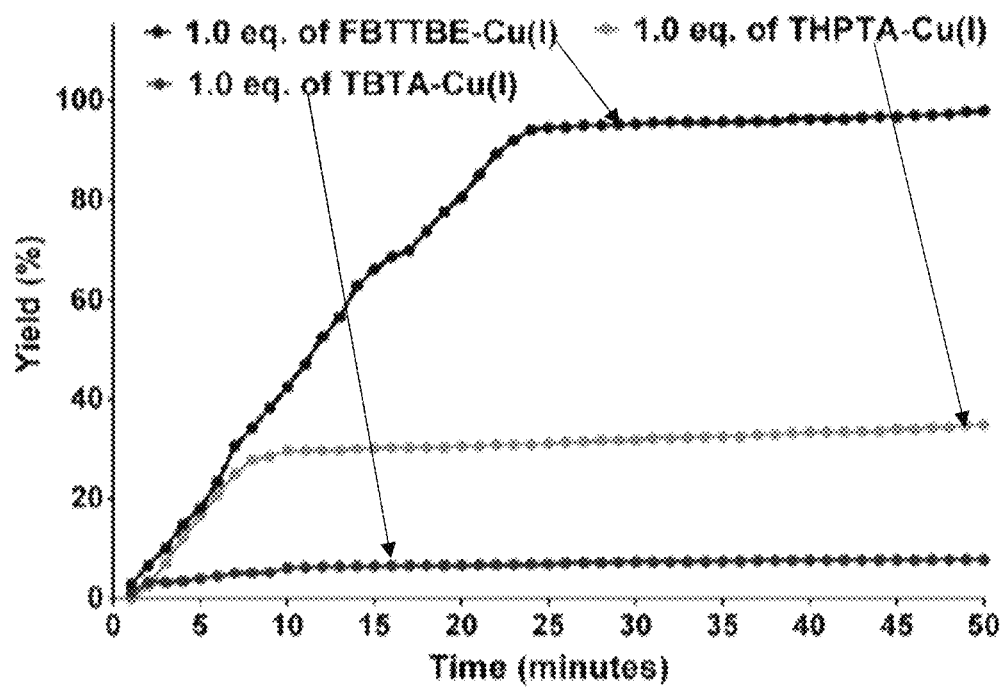
FIG. 5 shows Comparison Graph 3 shows a comparison of Cu(I) stabilizing ligands in the CuAAC between propargyl amine and 3-azido-7-hydroxycoumarin ([azidocoumarin]=10 μM; [propargyl amine]=15 μM, ligand: Cu(I) 1.5:1).

Comparison Graph 3 of FIG. 5 shows a comparison of Cu(I) stabilizing ligands in the CuAAC between propargyl amine and 3-azido-7-hydroxycoumarin ([azidocoumarin]=10 μM; [propargyl amine]=15 μM, ligand Cu(I)=1.5:1).

As discussed above, the fluorous-tag containing FTBTT ligand features a rapid F-SPE removal capability. Utilizing radioactive $^{64}Cu^{2+}$, the trapping efficiency of the fluorous resin was determined. In this experiment, $^{64}Cu^{2+}$ (100 μCi) was added to a non-radioactive $Cu^{2+}$ solution, and the resulting carrier-added $^{64}Cu^{2+}$ (200 M) was then mixed with 1.5 equiv. of FTBTT followed by 1.0 eq. of NaAA; the mixture was passed through the fluorous resin after a 5 min incubation. Over 99% of the radioactivity remained on resin, demonstrating that FTBTT-Cu(I) can be efficiently trapped. Therefore, it is anticipated that the removal of toxic copper species after CuAAC can be greatly simplified to a one-step filtration using FTBTT as the catalytic ligand.

The superior catalytic efficiency as well as the ease of separating toxic copper species when using FTBTT drove us to further investigate its application in preparing agents that could be used in living systems, such as a fluorescent dye attached peptide for fluorescent microscopy staining. Specifically, CuAAC between Cy3-azide and acetylene-AE105 (a urokinase-type plasminogen activator receptor, uPAR-targeted peptidic ligand) catalyzed by various Cu(I)-ligands was compared (Comparison Graph 4). The Cu(I)-FTBTT catalyzed CuAAC was complete in 5 min, whereas neither Cu(I)-TBTA nor Cu(I)-THPTA could achieve over 50% yield, even after incubating for 8 h. More importantly, both the Cu(I)-FTBTT catalyst and excess FTBTT ligand were rapidly removed by F-SPE. The resulting Cy3-AE105 conjugate was then used to stain human U87MG glioblastoma cells that overexpress uPAR.

In addition to the rapid and complete removal of toxic copper species and excellent catalytic efficiency, the FTBTT catalyst also demonstrated the capability of minimizing transchelation between non-radioactive copper and radiometals In 2006, Marik and Sutcliffe reported the first use of this method in preparing [$^{18}F$]fluoropeptides, and since then a large body of work employing the CuAAC has been presented in the preparation of F-based PET radiotracers. However, its application in radiometal-based probes still remains noticeably underdeveloped, possibly attributed to the transchelation between non-radioactive copper ions and those radiometals.

Even with an extremely low concentration of radiometal-containing reactants (e.g., 10-100 nM) and rapid decay of these radionuclides, a relatively large amount of the catalyst is required to ensure that the pmol-reactant reaction can complete within a relatively short time. This leads to not only difficulty in catalyst removal but also significant radiometal transchelation, resulting in significant decreases in specific activity of the corresponding radiopharmaceuticals.

Here, a click reaction used for preparing the $^{64}Cu$-labeled peptide was employed to evaluate the performance of FTBTT in addressing both removal of toxic copper and the radiometal transchelation problems. Specifically, azide modified CB-TE1K1P chelator ($N_3$-CB-TE1K1P) was incubated with $^{64}Cu$ for 5 min at 90° C., and the resulting $N_3$-($^{64}Cu$)CB-TE1K1P chelate was then conjugated to acetylene-AE105 peptide via CuAAC catalyzed by different ligands (Scheme 5). FTBTT exhibited much higher catalytic efficacy than either TBTA or THPTA (Comparison Graph 5). The rapid F-SPE removal capability was then investigated by comparing the UV peaks in the two HPLC traces of the above CuAAC mixtures before and after F-SPE purification. The retention time of the FTBTT/FTBTT-Cu(I) appeared to be 22.3 min according to the HPLC trace of the CuAAC mixture before F-SPE purification. After the F-SPE purification, it was found that the UV peak representing the FTBTT/FTBTT-Cu(I) completely disappeared, indicating that the catalyst was completely removed by the fluorous resin. In addition, the reaction mixture was also analyzed by the radio-HPLC to monitor potential transchelation. It was found that the radio-purity of the final product (retention time=20 min) was >98%, while there was no radioactive peak at either 1.5 or 22.3 min for Cu ions and FTBTT-Cu(I), respectively. Therefore, FTBTT can be regarded as an excellent ligand for the preparation of radiometal-based radiopharmaceuticals. The resulting ($^{64}Cu$)CB-TE1K1P-AE105 was subsequently used for PET/CT imaging of nude mice bearing subcutaneous U87MG xenografts that overexpress uPAR.

The FTBTT ligand has also been successfully applied in the rapid radiometal labeling of antibodies. Proteins are typically more sensitive to radiolabeling conditions such as pH, temperature and incubation time than small molecules and peptides. As a proof-of concept study, a monoclonal anti-EGFR antibody (cetuximab) was functionalized with an acetylene group using a slightly modified procedure from what was previously reported." The resulting acetylene-cetuximab was conjugated with N3-(64Cu) CB-TE1K1P via the Cu(I)-FTBTT catalyzed CuAAC under mild conditions (37° C. for 30 min) that would not denature the protein. The results were encouraging in that 50% of the ($^{64}Cu$)CB-TE1K1P was attached to cetuximab. The specific activity of the resulting $^{64}Cu$-labeled cetuximab was 10 μCi/p.g after purification by a Zeba desalting column. Together, these data demonstrated the broad applicability of the Cu(I)-FTBTT catalyst for radiometal labeling of peptides and antibodies.

In summary, a novel CuAAC ligand FTBTT has been successfully developed that not only demonstrated higher catalytic efficiency than two commercial available ligands (TBTA & THPTA), but also simplified the removal of toxic copper species after reactions, rendering it an ideal ligand for CuAAC. In addition, transchelation was avoided when applying FTBTT in preparing radiometal-based pharmaceuticals, broadening the application of CuAAC beyond $^{18}F$-chemistry. Although reactions presented here are primarily geared toward PET and molecular imaging, FTBTT can be applied in almost any CuAAC where the high reaction rate as well as the complete removal of copper species are desired.

Experimental Procedures

Materials:

3-Azido-7-hydroxycoumarin and Sulfo-Cyanine3 azide were purchased from AK scientific and Lumiprobe respectively. All other chemicals and solvents were purchased from Sigma-Aldrich 1. Synthesis of FTBTT Ligand:

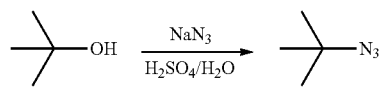

t-Butyl Azide (2):

A solution of H2SO4 (55 g, 0.56 mmol, 5.6 eq.) in 55 g H2O was prepared by the addition of 55 g H2SO4 to 55 g H2O over 10 min, with vigorously stirring in an ice cooled 250 mL flask. The solution was cooled to ≤5° C., and sodium azide (7.2 g. 0.11 mol) was slowly added over 10 min (maintaining the temperature ≤20° C. in order to preclude accidental volatilization of $HN_3$). When all of the NaN3 has dissolved, t-butyl alcohol (7.4 g. 0.1 mol) was added, and the resulting solution was stirred for 5 min and allowed to stand at room temperature for 24 h. t-Butyl azide floated to the top of the acid mixture was collected in a reparatory funnel, washed with 50 ml of 2 M NaOH to remove all traces of HN$_3$, dried over Na$_2$SO$_4$, and clear liquid was obtained as the product. $^1$H NMR complies with the reported value.

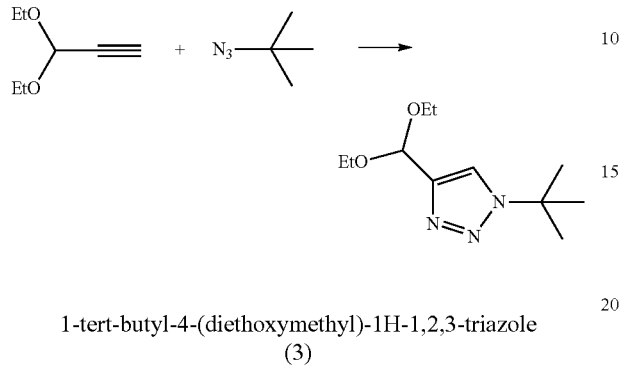

1-tert-butyl-4-(diethoxymethyl)-1H-1,2,3-triazole
(3)

To a 20-mL screw-capped scintillation vial equipped with a stirring bar were added 3,3-diethoxy-1-propyne (1.50 g, 11.8 mmol, 10 eq) and tert-butyl azide (1.34 g, 13.5 mmol, 1.15 eq) in 10 mL 1:1 mixture of tertbutyl alcohol and water Sodium bicarbonate (1.40 g, 16.7 mmol, 1.41 eq), copper(II) sulfate pentahydrate (0.143 g, 0.57 mmol, 5.0 mol %), and sodium ascorbate (0.47 g, 2.35 mmol, 20 mol %) were added to the mixture. The reaction was stirred overnight, and then EDTA (2 mL, 0.5 M, pH=8) was added. The resulting mixture was diluted with EtOAc (90 mL), washed with sat. aq NaHCO$_3$ (100 mL), water (50 mL), and brine (50 mL). The combined organic phases were dried over anhydrous MgSO$_4$. Solvent was removed and the residue was used in the next step without purification. $^1$H NMR complies with the reported value.

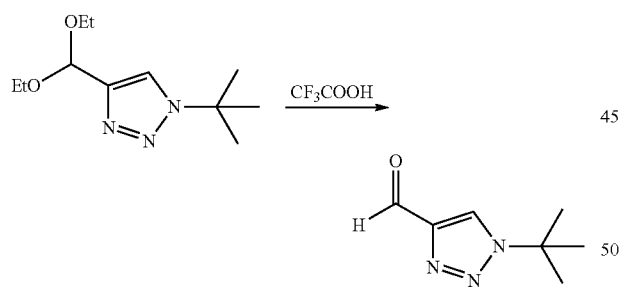

1-tert-butyl-1H-1,2,3-triazole-4-carbaldehyde (4)

To a 50-mL round bottom flask was added a solution of 1-tert-butyl-4-(diethoxymethyl)-1H-1,2,3-triazole (1.28 g, 5.63 mmol) in dichloromethane (6.0 mL), followed by addition of water (3.0 mL) and trifluoroacetic acid (1.0 mL) The reaction mixture was stirred vigorously under nitrogen for 3 h and then was diluted with EtOAc (100 mL), washed with sat aq NaHCO$_3$ (3×40 mL) and brine (40 mL). The combined organic phases were dried over anhydrous MgSO$_4$, filtered. Solvent was removed and the residue was used in the next step without purification. $^1$H NMR complies with the reported value.

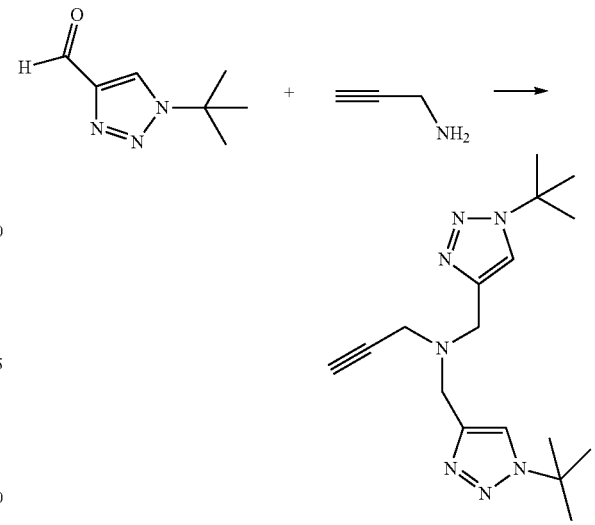

N, N-bis((1-tert-butyl-1H-1,2,3-triazol-4-371) methyl)prop-2-yn-1-amine (5)

To a 250-mL round bottom flask was added a solution of 1-tert-butyl-1H-1,2,3-triazole-4-carbaldehyde (2.47 g, 16.1 mmol, 2.2 eq) in dichloroethane, followed by addition of propargyl amine (361 mg, 72 mmol, 1.0 eq). To this mixture sodium triacetoxyborohydride (3.8 g, 17.9 mmol, 2.5 eq) was added in one portion with vigorous stirring. The reaction mixture was stirred at room temperature for 40 h. 1N H$_2$SO$_4$ (86 mL) was added to the reaction, and the mixture was stirred for 15 min. The pH was adjusted to >10 by addition of potassium carbonate. The reaction mixture was diluted with water (100 mL) and extracted with dichloromethane (3×300 mL). The organic layers were combined, dried over anhydrous MgSO$_4$, and filtered. Solvent was removed and the residue was purified on column to afford the product as a white powder. $^1$H NMR complies with the reported value.

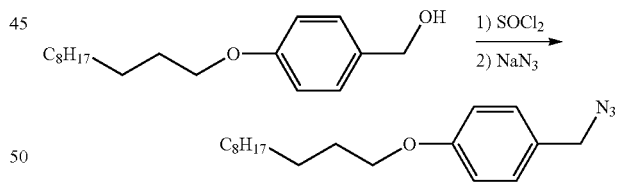

4-[3-(Perfluorooctyl)-1-propyloxyl]benzyl azide (7)

4-[3-(Perfluorooctyl)-1-propyloxy]benzyl alcohol (290 mg, 0.5 mmol) was dissolved in 1.0 mL DCM. Thionyl chloride (110 IA) and DMF (10 IA) were then added to the mixture. After stirred for 1 hour, the solvent was removed under reduced pressure. After lyophilization for 1 hour, the residue was dissolved in 20 mL THF/DMF (1.1) and NaN$_3$ (325 mg, 0.5 mmol) was added to the mixture. The mixture was stirred for 3 days at 60° C. Solvent was removed under reduced pressure. Product was extracted by DCM (100 ml) and washed with 60 mL NaHCO$_3$: Brine (1:1). Solvent was removed under reduced pressure and the residue was purified on column with EA:HEX (1:4) to afford the target product. The product was used in next step without characterization. ESI-MS, M/Z (M+H)+=610.52.

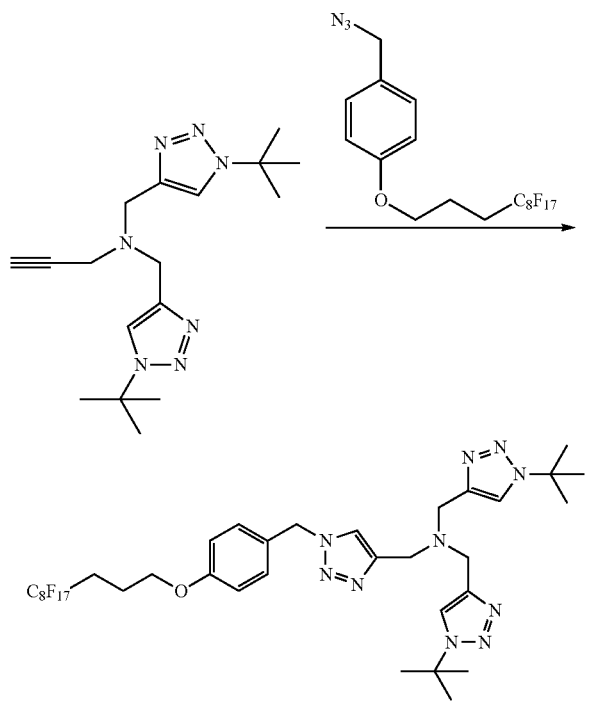

FTBTT (Fluorous Tagged -2-[4-{(Bis[(1-Tert-butyl-1H-1,2, 3-Triazol-4-yl) methyl]amino)methyl}-1H-1,2, 3-triazol-1-yl1) (8)

1-(azidomethyl)-4-(undecyloxy)benzene (100 mg, 0.16 mmol), N,N-bis((1-(tert-butyl)-1H-1,2,3-triazol-4-yl)methypprop-2-yn-1-amine (53 mg, 0.16 mmol), CuSO4.5H2O (12.5 mg, 0.05 mmol) and sodium ascorbate (40 mg, 0.20 mmol) were dissolved in t-BuOH/H$_2$O (1 1) in 2.0 mL and stirred overnight. Solvent was removed and the residue was purified on column with EA.HEX (1:4) to afford the target product $^1$H NMR (400 MHz, CDCl$_3$) δ 1.68 (18H, s, tert-butyl CH$_3$), 2.05-2.15 (2H, m, CH$_2$), 2.22-2.38 (2H, m, CH$_2$), 3.76 (6H, s, broad, NCH$_2$), 4.03 (2H, t, J=6 Hz, OCH$_2$), 5.46 (2H, s, NCH$_2$), 6.87 (2H, d, J=8.4 Hz, CH), 7.25 (2H, d, J=8.4 Hz, CH), 7.93 (3H, s, broad, CH). $^{13}$C NMR (100 MHz, CDCl$_3$) δ 20.5, 27.9, 30.0, 46.9, 47.0, 53.6, 59.3, 66.4, 115.0, 121.3, 124.0, 125.5, 127.2, 129.6, 158.8.

2. Synthesis of Acetylene-AE105 Peptide:

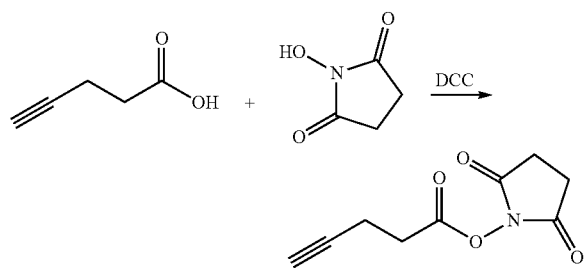

4-Pentynoic Acid Succinimidyl Ester:
Pentynoic acid (0.98 g, 10.0 mmol) and N-Hydroxysuccinimide (1.15 g, 10 mmol) were suspended in 200 mL of dry dichloromethane, and then N,N'-Dicyclohexylcarbodiimide (2.06 g, 10 mmol) was added. The reaction mixture was stirred at room temperature overnight, and then the white precipitate was filtered off. The filtrate was concentrated to afford the crude product. Pure 4-pentynoic acid succinimidyl ester was obtained as white solid after recrystallization from dichloromethane/diethylether. 111 NMR complies with the reported value.

Preparation of Acetylene-AE105 Peptide Conjugate:

To the solution of AE105 peptide (in dimethylformamide), 4-pentynoic acid succinimidyl ester (1.5 equiv.) was added, and followed by triethylamine (5.0 equiv.). The resulting mixture was stirred overnight at room temperature in the dark. The acetylene attached peptide conjugate was purified by HPLC (high performance liquid chromatography), and pure product was obtained as white powder after lyophilization overnight. ESI-MS, M/Z (M+H)+=1305.22.

3. Synthesis of Azide-CB TE1K1P:

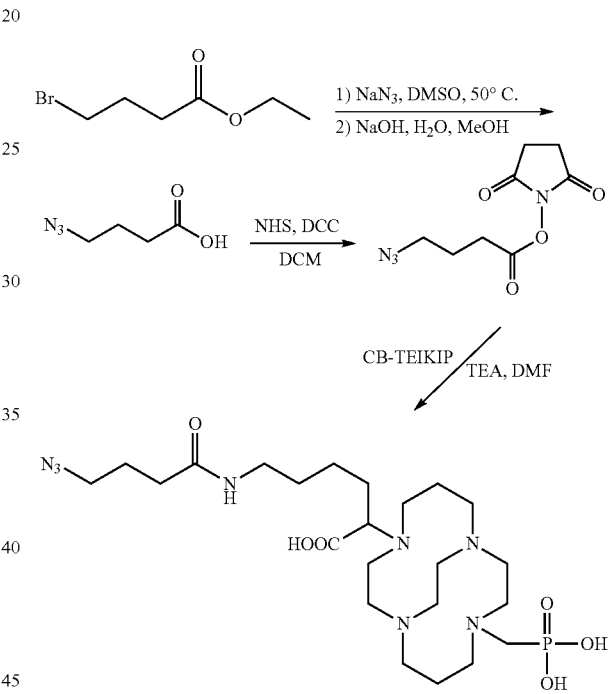

Chemical Formula: C$_{23}$H$_{45}$N$_8$O$_6$P
Exact Mass: 560,320

Azidobutyrate acid succinimidyl ester was prepared from ethyl 4-bromobutyrate as previously described, and CB-TE1K1P was synthesized following the published procedures. Azidobutyrate acid succinimidyl ester (56.5 mg, 250 μmop was added to the mixture of TEA (111 μl 800 μmol), CB-TE1K1P (45 mg, 100 μmol) and DMF (2.5 mL). The resulting mixture was stirred overnight, and then the solvent was removed under vacuum and the residue was purified using HPLC. The pure product was obtained as a white powder. ESI-MS, M/Z (M+H)+=561.31.

4. General Procedures for the CuAAC Reaction Using the Stabilizing Ligand:

Preparation of the Ligand FTBTT-Cu(I) Stock Solution:

15 mM of FTBTT in ethanol, was mixed with 10 mM of Cu(I) in water with the volume ratio of 1:1. Therefore, the molar concentration of FTBTT and Cu(I) was 7.5 mM and 5 mM respectively.

1). Preparation of the Fluorescence Dye Labeled Compounds:

Scheme 4. The click reaction between propargyl amine and 3-azido-7-hydroxycoumarin.

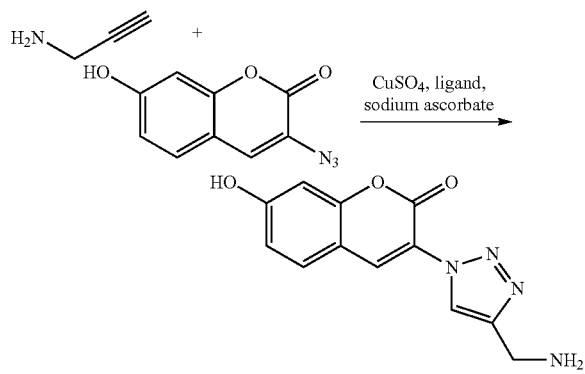

2). Preparation of Cy3 Attached AE105 Peptide with Various Cu(I) Stabilizing Ligands:

50 μL of azide-fluorescence dye (Sulfo-Cyanine3 azide, 5.0 mM in DMSO) and 50 μL of acetylene-AE105 (5.0 mM in 10% DMSO) were added to 375 μL of $NH_4OAc$ buffer (0.1 M, pH ~8.20), followed by 75 μL of the above FTBTT-Cu(I) stock solution. The reaction mixture was incubated for a given time, monitored by HPLC. Once all azide-fluorescence dye was converted to the product, the reaction solution was diluted with water, and then passed through the FluoroFlash SPE resin. The filtrate was collected as product, while the FTBTT and FTBTT-Cu(I) complex retained on the resin. ESI-MS, M/Z $(M+H)^+=2003.57$.

Figure 6:
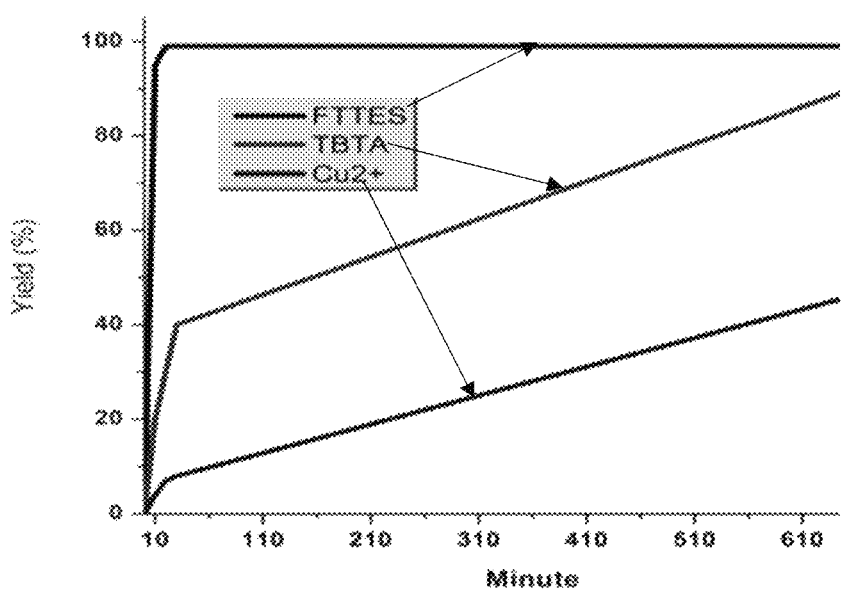
FIG. 6 shows Comparison Graph 4 illustrating a comparison of Cu(I) stabilizing ligands in CuAAC between Cy3-azide and acetylene-AE105.

Comparison Graph 4 of FIG. 6 shows a comparison of Cu(I) stabilizing ligands in CuAAC between Cy3-azide and acetylene-AE105.

3). Preparation of Cu-64 Labeled AE105 Peptide:

The radiometal (64Cu) labeling of chelator was conducted by incubating the azide-CB-TE1K1P and Cu in 0.1 M $NH_4OAc$ buffer (pH ~8.20) at 40° C. for 15 minutes, with the specific activity (SA) of 1.0 mCi/nmole. Then, 250 μCi of the resulting $^{64}Cu$ labeled azide-CB-TE1K1P was added to 0.5 nmole of the prepared acetylene-AE105, followed by the addition of 1.0 FAL of above FTBTT-Cu(I) stock solution. After incubated for a given time, 10~50 μCi of the reaction mixture was loaded into radio-HPLC to determine the radiolabeling yield. Once the radiolabeling yield was over 95%, the reaction solution was diluted with water, and then passed through the FluoroFlash SPE resin. The filtrate was collected as product, while the FTBTT and FTBTT-Cu(I) complex retained on the resin.

Figure 7:
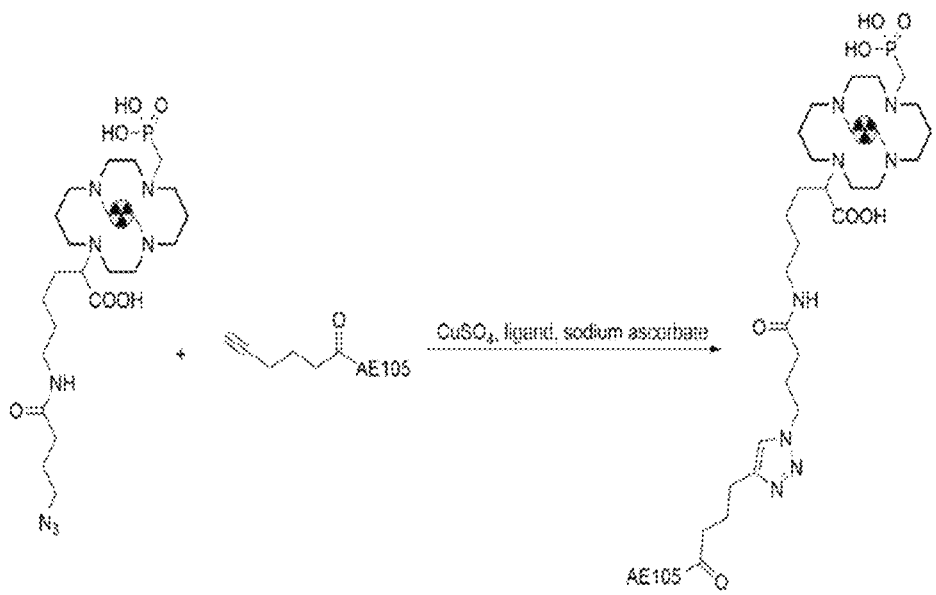
FIG. 7 shows Scheme 5 for the click reaction for the preparation of Cu-64 labeled AE105.

FIG. 7 shows Scheme 5 for the click reaction for the preparation of Cu-64 labeled AE105.

Figure 8:
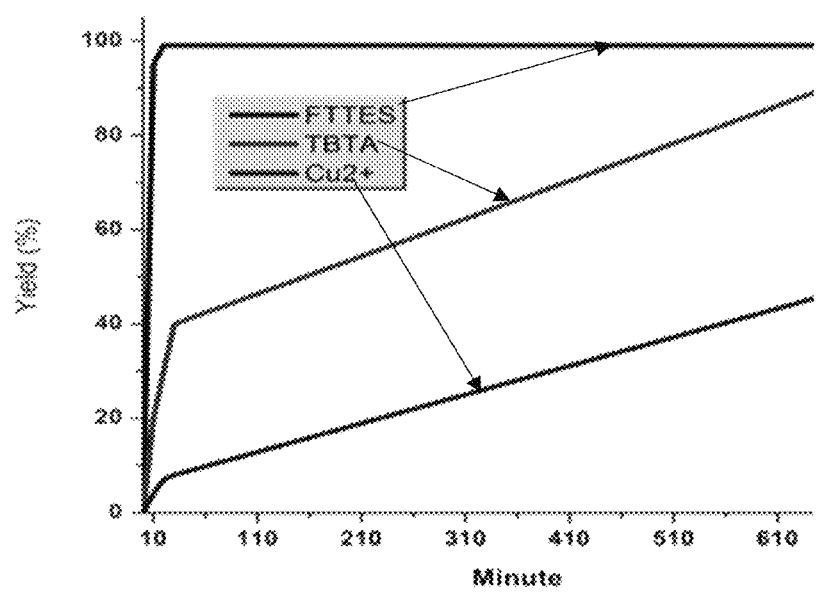
FIG. 8 shows Comparison Graph 5 illustrating a comparison of catalytic efficiency (ligand:Cu:NaAA-1.5:1:0.8) for the preparation of Cu-64 labeled peptide (SA=0.5 mCi/nmole).

Comparison Graph 5 of FIG. 8 shows a comparison of catalytic efficiency (ligand:Cu:NaAA=1.5:1:0.8) for the preparation of Cu-64 labeled peptide (SA=0.5 mCi/nmole).

4). Preparation of Cu-64 Labeled Cetuximab:

Azide-CB-TE1K1P was radiolabeled with 2.0 mCi of Cu-64 at 37° C. for 30 min, and the resulting $N_3$-$(^{64}Cu)$CB-TE1K1P (specific activity of 1.0 mCi/nmole) was then mixed with 100 ug of acetylene-cetuximab (prepared using the reported procedures). The click reaction started after the catalyst FTBTT-Cu(I) was added, and after incubating at 37° C. for 30 minutes, the FBTTBE-Cu(I) was then removed by passing through Fluorous-resin. In the filtrate, ~50% of $N_3$-(64Cu)CB-TE1K1P was attached to cetuximab, and over 90% radiopurity was obtained after the filtrate passed over Zaba desalting column.

5. Staining of U87MG Using AE105-Cy3:

Cells were seeded in an 8 well chamber slide (100,000 cells per well) 24 h prior to the experiment. Before the experiment, cells were washed twice with PBS, and added with culture medium. Then blocking agent (10 μg AE105) was added to half of the wells to determine in vitro non-specific uptake. After 1 h incubation, AE105-Cy3 (10 pmol per well) was then added to each well, and cells were incubated for another 2 h. Medium was then removed and cells were washed twice with PBS. After fixing the cells using 1% Paraformaldehyde, the nucleus was stained by DAPI. The slide was sealed and observed under fluorescence microscopy (40 ×, oil).

6. Small-Animal PET/CT Imaging Studies for AE105-64Cu-CBTE1K1P:

All animal studies were conducted under a protocol approved by the University of Pittsburgh Institutional Animal Care and Use Committee. U87MG xenograft tumor-bearing mice (n=3, 4 per group) were injected intravenously (lateral tail vein) with the prepared AE105-$^{64}$Cu-CBTE1K1P. Half of the mice received a dose that was premixed with AE105 (50 μg) for blocking. At 1 h and 4 h mice were anesthetized with 2% isoflurane, and small-animal PET/CT was performed. Static images were collected for 15 min. PET and CT images were co-registered with Inveon Research Workstation (IRW) software (Siemens Medical Solutions). PET images were reconstructed with the ordered-subsets expectation maximization 3-dimensional/maximum a posteriori probability algorithm, and the analysis of images was done using IRW.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A Cu(I)-Catalyzed Azide-Alkyne Cycloadditions (CuAAC) ligand comprising:
   a catalytic core, wherein the catalytic core comprises -2-[4-{bis[(1-tert-butyl-1H-1,2,3-tri-azol-4-yl)methyl] amino)methyl}-1H-1,2,3-triazol-1-yl]);
   a fluorous tag; and
   a linker binding the fluorous tag to the catalytic core.

2. A Cu(I)-Catalyzed Azide-Alkyne Cycloadditions (CuAAC) ligand comprising:
   a catalytic core;
   a fluorous tag; and
   a linker binding the fluorous tag to the catalytic core, wherein the linker comprises PEG.

3. A method for carrying out a Cu(I)-Catalyzed Azide-Alkyne Cycloaddition reaction, comprising:
   combining in a solution an alkyne-tagged component, an azide-tagged component and a Cu(I)-Catalyzed Azide-Alkyne Cycloadditions (CuAAC) ligand comprising: a catalytic core;
   a fluorous tag; and a linker binding the fluorous tag to the catalytic core;

filtering the solution through a solid phase extraction filter to remove Cu(I)-ligand catalyst and/or excess ligand, wherein the catalytic core comprises -2-[4-{bis[(1-tert-butyl-1H-1,2,3-tri-azol-4-yl)methyl]amino)methyl}-1H-1,2,3-triazol-1-yl]).

4. A method for carrying out a Cu(I)-Catalyzed Azide-Alkyne Cycloaddition reaction, comprising:

combining in a solution an alkyne-tagged component, an azide-tagged component and a Cu(I)-Catalyzed Azide-Alkyne Cycloadditions (CuAAC) ligand comprising: a catalytic core;

a fluorous tag; and a linker binding the fluorous tag to the catalytic core;

filtering the solution through a solid phase extraction filter to remove Cu(I)-ligand catalyst and/or excess ligand; and producing the alkyne-tagged component comprising an alkyne-bearing radiometal with a chelator selected from the group consisting of a NOTA, a DOTA, a CB-TE2A, a CB-DO2A, a 3p-C-DEPA, a TCMC, and Oxo-DO3A, a TETA, a TE2A, a CB-TE1A1P, a CB-TE2P, MM-TE2A, a DM-TE2A, a NETA, a TACN-TM, a DTPA, a 1B4M-DTPA, a CHX-A"-DTPA, a TRAP (PRP9), a NOPO, an AAZTA and derivatives (DATA), a HBED, a SHBED, a BPCA, a CP256, a Desferrioxamine (DFO), an $H_6$phospa, a PCTA, a HEHA, a PEPA, an $H_2$dedpa, an $H_4$octapa, an $H_2$azapa, an $H_5$decapa.

\* \* \* \* \*